(12) United States Patent
Rosenberg et al.

(10) Patent No.: US 7,479,550 B2
(45) Date of Patent: Jan. 20, 2009

(54) AMYLOID β GENE VACCINES

(75) Inventors: Roger N. Rosenberg, Dallas, TX (US); Stephen A. Johnston, Tempe, AZ (US); Bao-Xi Qu, Plano, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 11/445,936

(22) Filed: Jun. 2, 2006

(65) Prior Publication Data

US 2007/0280953 A1    Dec. 6, 2007

(51) Int. Cl.
*C07H 21/04* (2006.01)
*A01N 43/04* (2006.01)
*A61K 39/12* (2006.01)
*A61K 39/00* (2006.01)

(52) U.S. Cl. ............... 536/23.1; 514/44; 424/192.1; 424/186.1

(58) Field of Classification Search .............. None
See application file for complete search history.

(56) References Cited

U.S. PATENT DOCUMENTS

| | | | |
|---|---|---|---|
| 4,683,202 A | 7/1987 | Mullis | 435/91.2 |
| 5,717,058 A | 2/1998 | Matthews et al. | 530/328 |
| 5,928,906 A | 7/1999 | Koster et al. | 435/91.2 |
| 6,410,210 B1 | 6/2002 | Gabriel | 430/315 |
| 6,410,241 B1 | 6/2002 | Sykes et al. | 435/6 |
| 6,461,606 B1 | 10/2002 | Flotte et al. | 424/93.2 |
| 6,525,189 B1 | 2/2003 | Kim | 536/24.1 |
| 6,787,140 B1 | 9/2004 | Schenk | 424/185.1 |
| 6,900,018 B2 | 5/2005 | Sykes et al. | 435/6 |
| 7,018,833 B2 | 3/2006 | Sykes et al. | 435/320.1 |
| 7,018,836 B1 | 3/2006 | Price | 435/325 |
| 7,312,202 B2 | 12/2007 | Johnston et al. | 514/44 |
| 2002/0055173 A1 | 5/2002 | Parks et al. | 435/456 |
| 2002/0146733 A1 | 10/2002 | Sykes et al. | 435/6 |
| 2002/0150940 A1 | 10/2002 | Sykes et al. | 435/6 |
| 2002/0155508 A1 | 10/2002 | Sykes et al. | 435/7.2 |
| 2002/0160402 A1 | 10/2002 | Sykes et al. | 435/6 |
| 2003/0092614 A1 | 5/2003 | Herath et al. | 514/12 |
| 2003/0104356 A1 | 6/2003 | Berger | 435/5 |
| 2003/0129169 A1 | 7/2003 | Krohn et al. | 424/93.21 |
| 2003/0186424 A1 | 10/2003 | Roninson et al. | 435/235.1 |
| 2004/0091945 A1 | 5/2004 | Fitzer-Attas et al. | 435/7.2 |
| 2004/0138296 A1 | 7/2004 | Robertson et al. | 514/461 |

FOREIGN PATENT DOCUMENTS

| WO | WO 99/27944 | 6/1999 |
|---|---|---|
| WO | WO 2005/014041 | 2/2005 |

OTHER PUBLICATIONS

NCBI Genbank Accession # 1718342B.*
Uchiyama et al., Endosomal/lysosomal targeting of a single helper T-cell epitope of an intracellular bacterium by DNA immunisation induces a specific T-cell subset and Partial protective immunity in vivo, 2002, FEMS Microbiology Letters, vol. 216, pp. 91-97.*

Song et al., Sustained secretion of human alpha-1-antitrypsin from murine muscle transduced with adeno-associated virus vectors, 1998, PNAS, vol. 95, pp. 14384-14388.*

Genbank Accession # CAC67720, published Apr. 15, 2005.*

Bennett et al., "Cutting Edge: Adenovirus E19 Has Two Mechanisms for Affecting Class I MHC Expression," *J of Immunol*, 162:5049-5052, 1999.

Ciernik et al., "Induction of cytotoxic T lymphocytes and antitumor immunity with DNA vaccines expressing single T cell epitopes," *J Immunol*, 156:2369-2375, 1996.

Dahllof et al., "The Endoplasmic Reticulum Retention Signal of E3/19K Protein of Adenovirus-2 Is Microtubule Binding," *J Cell Biology*, 266:1804-1808, 1991.

Gabathuler and Kvist, "The Endoplasmic Reticulim Retention Signal of the E3/19K Protein of Adenovirus Type 2 Consists of Three Separate Amino Acid Segments at the Carboxy Terminus," *J Cell Biology*, 111:1803-1810, 1990.

Gabathuler et al., "Requirements for the association of adenovirus type 2 E3/19K wild-type and mutant proteins with HLA antigens," *J Virol.*, 64:3679-3685, 1990.

Hermiston et al., "Deletion mutation analysis of the adenovirus type 2 E3-gp19K protein: identification of sequences within the endoplasmic reticulum lumenal domain that are required for class 1 antigen binding and protection from adenovirus-specific cytotoxic T lymphocytes," *J Virol.*, 67:5289-5298, 1993.

Horn, "The Big Chill: Buying Time to Save Lives," In: Investigations Explinations and revelations taking place at the medical school, PITTMED, pp. 11, 2004.

Kaiser, "Study Links CSF and Brain Imaging for Identifying Dementia," *Applied Neurology*, vol. 2, No. 3, Mar. 2006.

Kim et al., "Immunization of Alzheimer model mice with adenovirus vectors encoding amyloid beta-protein and GM-CSF reduces amyloid load in the brain," *Neuroscience Letters*, 370:218-223, 2004.

Marques et al., "HIV-1 p55Gag encoded in the lysosome-associated membrane protein-1 as a DNA plasmid vaccine chimera is highly expressed, traffics to the major histocompatibility class II compartment, and elicits enhanced immune responses," *J Biol Chem*, 278:37926-37936, 2003.

(Continued)

*Primary Examiner*—Bruce Campell
*Assistant Examiner*—Benjamin P Blumel
(74) *Attorney, Agent, or Firm*—Fulbright & Jaworski

(57) ABSTRACT

The invention generally concerns compositions and methods for genetic vaccination with amyloid beta (Aβ) protein. Such vaccines may provide effective treatment for neurodegenerative disease such as Alzheimer's disease. Vaccination methods are can be used to induce a Th2 type immune response directed to Aβ. This immune response id shown to substantially reduce Aβ concentration and Aβ plaque size in an Alzheimer's model system.

5 Claims, 5 Drawing Sheets

OTHER PUBLICATIONS

Mejia, "Rapamycin Moonlights: What Makes an Immunosuppressant a Potentially Excellent Cancer Drug?" In: Investigations Explinations and revelations taking place at the medical school, PITTMED, pp. 10, 2004.
NCBI Accesion No. AJ293917.
NCBI Accession No. NC_001405.
NCBI Accession No. X95259.
NCBI Accession No. Y11260.
NCBI Accession No. Y16037.
Ohlson, "Seeing Alzheimer's: Compound Makes the Disease Visible in Living Patients," In: Investigations Explinations and revelations taking place at the medical school, PITTMED, pp. 9, 2004.
Okura et al., "Nonviral Aβ DNA vaccine therapy against Alzheimer's disease: Long-term effects and safety," *Proc Natl Acad Sci USA*, 103:9619-9624, 2006.
Qu et al., "Abeta42 gene vaccination reduces brain amyloid plaque burden in transgenic mice," *J Neurol Sci*, 244:151-158, 2006.
Qu et al., "Gene vaccination to bias the immune response to amyloid-beta peptide as therapy for Alzheimer disease," *Arch Neurol*, 61:1859-1864, 2004.
Reinberg, "Brain Scan May Spot Alzheimer's Progression: In the future, new technologies could identify who's at risk, researchers say," *HealthDay Reporter*, Nov. 15, 2005.
UniProt Accession No. P68978.
UniProt Accession No. P68979.
UniProt Accession No. Q67811.
Zhang et al., "A novel recombinant adeno-associated virus vaccine reduces behavioral impairment and beta-amyloid plaques in a mouse model of Alzheimer's disease," *Neurobiology of Disease*, 14:365-379, 2003.
Barry et al., "Protection against mycoplasma infection using expression-library immunization," *Nature*, 377(6550):632-635, 1995.
Breathnack and Chambon, "Organization and expression of eucaryotic split genes coding for proteins," *Annu. Rev. Biochem.*, 50:349-383, 1981.
Burke et al., "The DPE, a conserved downstream core promoter element that is functionally analogous to the TATA box," *Cold Harbor Symposia on Quantitative Biology*, vol. LXIII, 75-82, The Mechanisms of Transcription, 1998.
Faisst and Meyer, "Compilation of vertebrae-encoded transcription factors," *Nucleic Acids Research*, 20(1):3-26, 1992.
Fujita et al., "Delimitation and properties of DNA sequences required for the regulated expression of human interferon-β gene," *Cell*, 41(2):489-496, 1985.
Fynan et al., "DNA vaccines: protective immunizations by parenteral, mucosal, and gene-gun inoculations," *Proc. Natl. Acad. Sci., USA*, 90:11478-11482, 1995.
Graves et al., "Homologous recognition of a promoter domain common to the MSV LTR and the HSV tk gene," *Cell*, 44(4):565-576, 1986.
Gronostajski, "Site-specific DNA binding of nuclear factor I: effect of the spacer region," *Nucleic Acids Research*, 15(14):5545-5559, 1987.
Harms and Splitter, "Interferon-γ inhibits transgene expression driven by SV40 or CMV promoters but augments expresion driven by the mammalian MHC I promoter," *Hum. Gene Ther.*, 6(10):1291-1297, 1997.
Hoag et al., "Gene therapy expression vectors based on the clotting Factor IX promoter," *Gene Ther.*, 6:1584-1589, 1999.

Hu et al., "Transcriptional factor AP-4 contains multiple dimerization domains that regulate dimer specificity," *Genes Dev.*, 4(10):1741-1752, 1990.
Kadonaga et al., "Isolation of cDNA encoding transcription factor Sp1 and functional analysis of the DNA binding domain," *Cell*, 51(6):1079-1090, 1987.
Liu and Green, "A specific member of the ATF transcription factor family can mediate transcription activation by the adenovirus E1a protein," *Cell*, 61(7):1217-1224, 1990.
McDonnell and Askari., "Molecule medicine," *New Engl. J. Med.*, 334(1):42-45, 1996.
Mitchell and Tijian, "Transcriptional regulation in mammalian cells by sequence-specific DNA binding proteins," *Science*, 245(4916):371-378, 1989.
Morral et al., "Immune responses to reporter proteins and high viral dose limit duration of expression with adenoviral vectors: comparison of E2a wild type and E2a deleted vectors," *Hum. Gene Ther.*, 8:1275-1286, 1997.
Pardoll et al., "Exposing the immunology of naked DNA vaccines," *Immunity*, 3:165-169, 1995.
Perlmann et al., "Determinants for selective RAR and TR recognition of direct repeat HREs," *Genes Dev.*, 7B:1411-1422, 1993.
Pollock et al., "Human SRF-related proteins: DNA-binding properties and potential regulatory targets," *Genes Dev.*, 5(12A):2327-2341, 1991.
Qin et al., "Promoter attenuation in gene therapy: interferon-γ and tumor necrosis factor-α inhibit transgene expression," *Hum. Gene Ther.*, 8(17):2019-2029, 1997.
Qu et al., "Abeta42 gene vaccine prevents Abeta42 deposition in brain of double transgenic mice," *J. Neurological Sci.*, 260:204-213, 2007.
Ritter et al., "Stimulatory and inhibitory action of cytokines on the regulation of hCMV-IE promoter activity in human endothelial cells," *Cytokine*, 12(8):1163-1170, 2000.
Robinson, "DNA based vaccines: new possibilities for disease prevention and treatment," *Can. Med. Assoc. J.*, 152(10):1629-1632, 1995.
Ruvkun and Finney, "Regulation of transcriptional and cell identity by POU domain proteins," *Cell*, 64(3):475-478, 1991.
Smale and Baltimore, "The 'initiator' as a transcription control element," *Cell*, 57(1):103-113, 1989.
Spooner et al., "DNA vaccination for cancer treatment," *Gene Therapy*, 2:173-180, 1995.
Struhl, "Yeast transcriptional regulatory mechanisms," *Ann. Rev. Genet.*, 29:651-674, 1995.
Tanaka et al., "Recognition DNA sequences of interferon regulatory factor 1 (IRF-1) and IRF-2, regulators of cell growth and the interferon system," *Mol. Cell. Biol.*, 13(8):4531-4538, 1993.
Virbasius, "NRF-1, an activator involved in nuclear-mitochondrial interactions, utilizes a new DNA-binding domain conserved in a family of developmental regulators," *Genes Dev.*, 7(12A):2431-2445, 1992.
Wahren et al., "HIV subtypes and recombination strains—strategies for induction of immune responses in man," *Vaccine*, 20:1988-1993, 2002.
Williams and Tijian, "Analysis of the DNA-binding and activation properties of the human transcription factor AP-2," *Genes Dev.*, 5(4):670-682, 1991.
Yen et al., "An alternative spliced form of FosB is a negative regulator of transcriptional activation and transformation by Fos proteins," *Proc. Natl. Acad. Sci., USA*, 88(12):5077-5081, 1991.

* cited by examiner

SEQUENCE LISTING

```
<160> NUMBER OF SEQ ID NOS: 10

<210> SEQ ID NO 1
<211> LENGTH: 48
<212> TYPE: PRT
<213> ORGANISM: Mus musculus

<400> SEQUENCE: 1

Ile Gln Thr Val Lys Val Ser Val Ser Ala Ala Thr Leu Gly Leu Gly
1               5                   10                  15

Phe Ile Ile Phe Cys Val Gly Phe Phe Arg Trp Arg Lys Ser His Ser
            20                  25                  30

Ser Ser Tyr Thr Pro Leu Ser Gly Ser Thr Tyr Pro Glu Gly Arg His
        35                  40                  45

<210> SEQ ID NO 2
<211> LENGTH: 42
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 17
<212> TYPE: PRT
<213> ORGANISM: Adenovirus Type 2

<400> SEQUENCE: 3

Met Arg Tyr Met Ile Leu Gly Leu Leu Ala Leu Ala Ala Val Cys Ser
1               5                   10                  15

Ala

<210> SEQ ID NO 4
<211> LENGTH: 112
<212> TYPE: PRT
<213> ORGANISM: Artificial
<220> FEATURE:
<223> OTHER INFORMATION: Chimeric fusion protein

<400> SEQUENCE: 4
```

-continued

```
Met Gly Tyr Met Ile Leu Gly Leu Leu Ala Leu Ala Ala Val Cys Ser
1               5                   10                  15

Ala Ala Thr Arg Asp Ala Glu Phe Arg His Asp Ser Gly Tyr Glu Val
            20                  25                  30

His His Gln Lys Leu Val Phe Phe Ala Glu Asp Val Gly Ser Asn Lys
        35                  40                  45

Gly Ala Ile Ile Gly Leu Met Val Gly Gly Val Val Ile Ala Arg Ser
        50                  55                  60

Ile Gln Thr Val Lys Val Ser Val Ser Ala Ala Thr Leu Gly Leu Gly
65                  70                  75                  80

Phe Ile Ile Phe Cys Val Gly Phe Phe Arg Trp Arg Lys Ser His Ser
                85                  90                  95

Ser Ser Tyr Thr Pro Leu Ser Gly Ser Thr Tyr Pro Glu Gly Arg His
            100                 105                 110
```

<210> SEQ ID NO 5
<211> LENGTH: 18
<212> TYPE: PRT
<213> ORGANISM: Adenovirus Type 5

<400> SEQUENCE: 5

```
Met Ile Arg Tyr Ile Ile Leu Gly Leu Leu Thr Leu Ala Ser Ala His
1               5                   10                  15

Gly Thr
```

<210> SEQ ID NO 6
<211> LENGTH: 19
<212> TYPE: PRT
<213> ORGANISM: Adenovirus Type 3

<400> SEQUENCE: 6

```
Met Gly Ala Ile Leu Val Val Val Ala Leu Leu Ser Leu Leu Gly Leu
1               5                   10                  15

Gly Ser Ala
```

<210> SEQ ID NO 7
<211> LENGTH: 19
<212> TYPE: PRT
<213> ORGANISM: Adenovirus Type 7

<400> SEQUENCE: 7

```
Met Gly Ala Ile Leu Val Leu Leu Ala Leu Leu Ser Leu Leu Gly Leu
1               5                   10                  15

Gly Ser Ala
```

<210> SEQ ID NO 8
<211> LENGTH: 19
<212> TYPE: PRT
<213> ORGANISM: Adenovirus Type 35

<400> SEQUENCE: 8

```
Met Gly Pro Ile Leu Val Leu Leu Val Leu Leu Ser Leu Leu Glu Pro
1               5                   10                  15

Gly Ser Ala
```

<210> SEQ ID NO 9
<211> LENGTH: 19
<212> TYPE: PRT
<213> ORGANISM: Adenovirus Type 11

```
<400> SEQUENCE: 9

Met Gly Pro Ile Leu Val Leu Leu Val Leu Leu Ser Leu Leu Glu Pro
1               5                   10                  15

Gly Ser Ala

<210> SEQ ID NO 10
<211> LENGTH: 18
<212> TYPE: PRT
<213> ORGANISM: Artificial
<220> FEATURE:
<223> OTHER INFORMATION: Modified adenovirus type 2 E3L sequence

<400> SEQUENCE: 10

Met Gly Tyr Met Ile Leu Gly Leu Leu Ala Leu Ala Ala Val Cys Ser
1               5                   10                  15

Ala Ala
```

US 7,479,550 B2

AMYLOID β GENE VACCINES

This invention was made with government support under grant number P30AG12300 awarded by the National Institutes of Health. The government has certain rights in the invention.

BACKGROUND OF THE INVENTION

I. Field of the Invention

The invention relates generally to the fields of neurology and immunology. Specifically, the invention concerns nucleic acid vaccines for treating and preventing Alzheimer's disease.

II. Description of Related Art

Alzheimer's disease (AD) is the most common cause of dementia, and currently there is no cure or effective treatment to prevent its progression. The cause of AD has been associated with the accumulation, aggregation, and deposition of amyloid beta peptides (Aβ) in cerebral cortex, hippocampus, and other subcortical structures (Selkoe, 2001; Rosenberg, 2000). Aβ is derived proteolytically from a glycosylated membrane protein known as beta-amyloid precursor protein or APP (Haass et al., 1992; Shoji et al., 1992). APP is ubiquitously expressed but is expressed at the highest levels in the central nervous system (Lahiri & Ge, 2004; Fox et al., 1997). The processed Aβ in brain is 39 to 43 amino acids in length with the major species being 40 and 42 amino acids (Aβ40 and Aβ42, respectively). In particular, the aggregated form of Aβ42 has been identified to play a major role in the initiation of neuropathology of AD (Iwatsubo et al., 1994; Iwatsubo et al., 1995; Yankner, 1996).

In recent years, reduction in the level of Aβ in brain has become a major therapeutic goal in prevention and treatment of AD. In transgenic mice carrying mutations causal of AD, reduction of the amyloid burden in brain and cognitive improvement have been achieved by active immunization of these mice with Aβ42 peptide or by infusion of anti-Aβ antibodies (Selkoe, 1999; Monsonego and Weiner, 2003; Schenk et al., 1999; Morgan et al., 2000; DeMattos et al., 2001). These results lead to a clinical trial of patients with Alzheimer's disease that was conducted by active Aβ42 peptide immunization. Unfortunately, the trial was halted due to the complications associated with cytotoxic T lymphocyte (CTL) mediated meningoencephalitis that occurred in about 6% of immunized AD patients (Schenk, 2002; Rosenberg, 2005). Nonetheless, neuropsychological testing of immunized patients showed some slowing of cognitive loss in a subset of patients who exhibited significant anti-Aβ antibody production and subsequent Aβ plaque reduction and clearance upon post-mortem examination (Kotilinek et al., 2002; Hock et al., 2003; Sorbi, 2005; Fox et al., 2005 and Gilman et al., 2005).

A variety of Aβ vaccine strategies have been proposed in the art. For example, U.S. patent publns. 2004/0091945 and 2004/0138296 concern Aβ peptide vaccine compositions for the treatment AD. Peptide Aβ vaccines are also discussed in PCT publication WO 99/27944. However, previous peptide vaccination strategies have resulted in Aβ specific Th1 type immune responses and CTL mediated meningoencephalitis. It has also been suggested that DNA vaccination may be a possible approach to Aβ vaccination U.S. Pat. No. 6,787,140 and PCT publication WO 2005/014041. However, it was not clear how such genetic vaccines might stimulate an improved immune response profile (i.e. a Th2 type response) or what kinds of genetic vaccines would be the most effective. Thus, to date there has not been described an Aβ gene vaccine that can induce a robust Th2 type immune response that results in Aβ plaque reduction.

SUMMARY OF THE INVENTION

The instant invention overcomes deficiencies in the prior art by providing methods and compositions for treating and/or preventing Alzheimer's disease by administration of an Aβ gene vaccine. In general, the invention concerns genetic amyloid beta (Aβ) vaccines that induce a Th2 type immune response. For example, in one embodiment of the invention, there is provided a method for stimulating a Th2 immune response against an Aβ polypeptide in an animal, the method comprising administering to the animal an Aβ gene vaccine.

Thus, in some embodiments, the invention concerns stimulating a Th2 type immune response, or more specifically a Th2 immune response directed against Aβ. Such a Th2 immune response may in, some instances, be characterized by cytokines that are secreted from Th2 type immune cells. For example, a Th2 immune response may involve an increase in serum levels of IL-4, IL-5 and/or IL-10. In some cases, a Th2 immune response may be indicated by production of Th2 type of immunoglobulin molecules such as, a IgG1 subtype antibody response.

Conversely, in certain embodiments of the invention, it is contemplated that an Aβ gene vaccine will elicit only a weak or minimal Th1 immune response. Indeed, in certain cases, an Aβ gene vaccine may produce an undetectable Th1 immune response. For example, Th1 immune cells are known to produce certain cytokines such as IL-2, IFN-γ and lympotoxin/TNF-β. Thus, in certain cases, an Aβ gene vaccine of the invention will not significantly elevate serum levels of such Th1 cytokines. In yet further embodiments, a vaccine of the invention does not produce significant numbers Aβ specific CTLs. For instance, following vaccination CTLs may not be detectable by Aβ specific ELISPOT assay (e.g. for IFN-γ) or by chromium release assay. Therefore, in some instances the invention provides a method for treating or preventing AD by administering a Aβ gene vaccine wherein, the vaccine produces very few or essentially no Aβ specific CTLs. Furthermore, in some cases, an Aγ gene vaccine of the invention may be defined as not producing pathologic brain inflammation.

In some embodiments of the invention, an immune response to an Aβ gene vaccine is monitored after vaccination. For example, the immune response may be monitored by measuring the concentrations of immune cells, cytokines and/or antibodies in the blood of vaccinated animals. A variety of methods, well known to those in the art, may be used to monitor an immune response in animals. For example, immune cells of any particular type may the counted by simple microscopy, by ELISA or by fluorescence activated cell sorting (FACS). Cytokine concentrations, in some cases, can be determined by ELISA, Western blot or RNase protection assay. Similarly, in some cases, concentration of various immunoglobulin isoforms may be determined by ELISA. Thus, following vaccination, the immune response to the vaccine can be characterized. These methods may in some instances be used to determine the next step in a therapy or preventive regimen. For example, if an immune response is found to be weak the Aβ gene vaccine may be administered in additional doses or quantities (e.g., administering an increased mass of nucleic acid) or a further therapy that stimulates the immune system may be applied. In another example, if an immune response is found to stimulate Th1 immune cells then therapy may be discontinued or additional compositions that stimulate a Th2 immune response by be applied in combination with vaccination.

In certain additional embodiments, a method of administering an Aβ gene vaccine may further comprise administering a immune modifier. An immune modifier may be administered before, after or essentially simultaneously with an Aβ gene vaccine. In some cases, the immune modifier may be a general immune response stimulator or adjuvant. However, in certain embodiments, an immune modifier may specifically stimulate a Th2 immune response or suppress a Th1 immune response. Thus, in certain very specific embodiments, the immune modifier may be IL-4, IL-5, IL-10 or interferon regulatory factor 1 (IRF-1) (Sasaki et al., 2002). Immune modifiers may be administered as a polypeptide or in some cases as a nucleic acid capable of expressing a particular immune modifier. Thus, in some very specific embodiments, nucleic acids encoding one or more immune modifiers may be administered simultaneously with an Aβ gene vaccine.

Methods or compositions of the invention may be used to treat or prevent late onset or early onset Alzheimer's disease. Thus, it is contemplated that a vaccine of the invention, in some instances, will be administered to an animal that has been diagnosed with Alzheimer's disease, such as a human that has been diagnosed by cognitive testing. In certain other cases, an Aβ gene vaccine may be administered to an animal as a preventative. For example, such a vaccine may be administered to a human once the human has reached a certain age, such as 30, 35, 40, 45, 50, 55, 60 or more years of age. In some additional cases, an Aβ gene vaccine may be administered to an animal that has an increased risk for developing Alzheimer's disease. For example, in certain cases, a method for vaccinating an animal against Alzheimer's disease may involve first testing the animal for an Alzheimer's associated marker. In some simple examples the testing of an animal for an Alzheimer's associated marker may involve determining if the animal has a has a genetic or family history of the disease. In another example, an Alzheimer's associated marker may be a genetic mutation associated with Alzheimer's disease, detection of plaques in the brain or the presence of elevated Aβ protein in the blood. For example, an Alzheimer's associated marker may be a genetic mutation in an APP, Presenilin 1, Presenilin 2 or Apolipoprotein E gene. In yet a further embodiment, an Aβ vaccine of the invention may be administered to an animal that already has detectable Aβ plaques in their brain, such as an animal diagnosed using positron emission tomography (PET) detection of Pittsburgh compound B (PIB) (Klunk et al, 2004). Thus, in some aspects of the invention an Aβ gene vaccine is administered to selected group of individuals that have an elevated risk for developing Alzheimer's disease.

In yet further embodiments, an Aβ gene vaccine may be defined by its effect on Aβ in an animal. For example, in some aspects of the invention an Aβ gene vaccine reduces the quantity, size or mass of amyloid plaques in the brain of the animal. In some cases, assessment of amyloid plaques may be accomplished via a postmortem analysis of brain tissue. However, it is contemplated that PET detection of PIB may be used to assess plaque regression as described in Klunk et al., 2004 and U.S. Pat. Nos. 6,114,175, 6,168,776 and 6,417, 178).

An Aβ gene vaccine may be administered to an animal by a variety of protocols. For instance, an Aβ nucleic acid may be introduced into a host cell by use of a cationic polymer (e.g., PEI), a liposome or a viral vectors. In still other embodiments, an Aβ gene vaccine may be administered by ballistic methods such as a gene gun. Thus, methods of the invention may comprise administration of an Aβ gene vaccine by intradermal, transdermal, parenteral, intravenous, intramuscular, intranasal, subcutaneous, percutaneous, intratracheal, intraperitoneal, intratumoral, perfusion, lavage, direct injection, or oral administration. In some very specific cases, an Aβ gene vaccine is administered via intramuscular ballistic methods, such as with a gene gun (e.g., a Helios gene gun available from Bio-Rad may be employed).

In still further embodiments of the invention, an Aβ gene vaccine may be administered two or more times. For example, the vaccine may be administered 1, 2, 3, 4, 5, 6, 7, 8, 9, 10, 15, 20, 25 or more times or any range derivable therein. Multiple administrations of an Aβ gene vaccine may be separated by any period of time, for example 1 or 2 weeks or one or more months or even by a year or more. For example, it is contemplated that an Aβ gene vaccine booster may be given annually. Additionally, an Aβ gene vaccine may be defined by the amount of nucleic acid encoding Aβ that is administered. For example, about or at least about 1, 2, 3, 4, 5, 6, 7, 8, 9, 10, 15, 20, 25, 30, 35, 40, 45, 50, 60, 70, 80, 90, 100, 150, or more μg of nucleic acid per administration may be used.

In some specific embodiments, there is provided a nucleic acid that may be used for Aβ gene vaccination. A nucleic acid of the invention may encode a fusion protein comprising an endoplasmic reticulum (ER) localization signal and an Aβ polypeptide. In some cases, a nucleic acid of the invention may be a RNA or DNA molecule. For example, the nucleic acid may be a mRNA molecule that can be expressed in mammalian cells, such as a capped and polyadenylated mRNA encoding an Aβ fusion protein. In certain other aspects, the nucleic acid may be a DNA molecule such as a DNA expression vector. In this instance the DNA molecule may additionally comprise elements for replication of the DNA in prokaryotic or eukaryotic cells or elements that facilitate expression of the Aβ fusion protein in mammalian cells. For example, the vector may comprise elements such as a promoter, enhancer and/or polyadenylation signal. In certain very specific examples a DNA vector may comprise a CMV or SP72 promoter sequence (U.S. Publn. 2004/0171573). For instance, a DNA vector of the invention may be a plasmid capable of replicating in bacterial cells and capable of expressing an Aβ fusion protein in mammalian cells.

In yet a further aspects of the invention, an Aβ fusion protein may comprise an ER localization signal, an Aβ polypeptide and a endosome targeting signal, such as a lysosome targeting signal. A variety of lysosomal targeting signals may be used according to the invention and their function is well known in the art. For example, a lysosome targeting signal may be the lysosomal targeting signal from the firefly luciferase protein. In some specific cases, a lysosome targeting sequence may be an MHC class II targeting sequence such as the sequence from a lysosome-associated membrane protein (Chen et al., 1985). For example, the endosome targeting sequence may comprise the sequence set forth in SEQ ID NO: 1 or a derivative thereof. In some very specific cases, an Aβ fusion protein of the invention may comprise, from amino terminus to carboxyl terminus (1) an ER localization signal, (2) an Aβ polypeptide and (3) an endosomal targeting signal, wherein additional amino acids may be between any of domains 1, 2 or 3.

As used herein the term Aβ polypeptide sequence may refer to any processed mammalian APP amino acid sequence. However, in certain aspects of the invention, the Aβ amino acid sequence is a human amino acid sequence. For example, the Aβ polypeptide may comprise an amino acid sequence that is about or at least about 70, 75, 80, 85, 90 or 95% identical to SEQ ID NO: 2. Thus, in certain specific cases, the Aβ polypeptide comprises human Aβ42 as given in SEQ ID NO: 2. Additionally, it will be understood that in certain cases an Aβ polypeptide may be a fragment of Aβ42, for example, amino acids 17-42 of SEQ ID NO: 2. Thus, in certain aspects, an Aβ polypeptide of the invention is an any amino acid sequence capable of eliciting an immune response that recognizes the Aβ42 polypeptide (e.g., an antibody that binds to Aβ42).

Thus, it will be understood that in certain cases an Aβ gene vaccine of the invention will produce antibodies to a particular Aβ epitope. For example, an Aβ gene vaccine may elicit an antibody response against an Aβ epitope between amino acids 1-16, 17-28 or 28-42 of Aβ42. In some very specific examples, the Aβ gene vaccine may produce a IgG1 immune response in an animal wherein the antibodies bind to an epitope in amino acids 1-16, 17-28 or 28-42 of Aβ42. Thus, an Aβ gene vaccine may, in some instances, be defined by the Aβ epitope recognized by antibodies elicited by the vaccine.

As described above, in certain aspects of the invention there is provided an Aβ fusion protein comprising and ER localization signal. In some embodiments of the invention, the ER localization signal is a signal other than the human alpha-1 antitrypsin leader. For instance, the ER localization signal may be the signal from an adenoviral E3 leader (E3L) sequence. In some very specific examples, the E3L sequence may be a sequence from a group B (e.g., Ad3, Ad7, Ad35 or Ad11) or group C adenovirus (e.g., Ad2 or Ad5). Thus, in certain aspects of the invention the E3L sequence will be SEQ ID NO: 3 or any of SEQ ID NOS: 5-9. In still further aspects, the ER localization signal may be modified adenoviral E3L sequence, for example an E3L sequence wherein the coding region is modified to improve the translation initiation codon context (i.e., Kozak consensus (Kozak, 1986; Kozak, 1987; Kozak 1989) thereby enhancing expression of the fusion protein. Such a modified adenoviral E3L may, for instance, be the sequence set forth in SEQ ID NO: 10 and exemplified herein. Thus, in some very specific embodiments of the invention, an Aβ fusion protein of the invention comprises from a amino terminus to carboxyl terminus Ad2 E3L (e.g., SEQ ID NO: 3 or SEQ ID NO: 10)-Aβ42 and the endosomal targeting sequence of SEQ ID NO: 1. Therefore, in certain cases, an Aβ fusion protein may comprise the sequence set forth in SEQ ID NO 4.

Embodiments discussed in the context of a methods and/or composition of the invention may be employed with respect to any other method or composition described in this application. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings are part of the present specification and are included to further demonstrate certain aspects of the present invention. The invention may be better understood by reference to the drawings in combination with the detailed description of specific embodiments presented herein.

FIG. 4A-H: Reduction of Aβ deposition in frontal cortex of 15-month-old APPswe/PS1ΔE9 mice immunized with Aβ42 gene vaccination (administered 11 times). Cryostat sections of the frozen frontal cortex are labeled with anti-Aβ42 antibody followed by a fluorescently labeled second antibody. Images of each mouse brain are obtained by confocal microscopy at 40× magnification. The upper panel images are taken from four control mice (A and B, vector only and C and D, vector with Aβ16) with large multiple plaques being seen scattered in all cortical areas. The lower panels of images (E-H) are from four treated (vector with Aβ42) mice with much smaller and fewer plaques. There is no significant difference in plaque volume in vector only control mice or control mice with Aβ16.

FIG. 5A-H. Reduction of Aβ deposition in hippocampus of 15-month-old APPswe/PS1ΔE9 mice immunized with Aβ42 gene vaccination for (administered 11 times). Paraffin-embedded sections of paraformaldehyde-fixed mice brain are labeled with anti-Aβ42 antibody followed by a fluorescently labeled second antibody. Images of each mouse brain are obtained by confocal microscopy at 40× magnification. The upper panel images are taken from four control mice (A and B, vector only; C and D, vector with Aβ16) with large multiple plaques being seen scattered in brain areas. The lower panels of images are from four treated (vector with Aβ42) (E-H) mice. The treated mice exhibit smaller and fewer plaques. There is no significant difference in plaque volume in vector only control mice or control mice with Aβ16.

DETAILED DESCRIPTION OF THE INVENTION

Recent clinical trails have explored methods for treating Alzheimer's disease by inducing an immune response against the Aβ polypeptide. These trails yielded some encouraging data, in that, patients with significant Aβ antibody response exhibited slowed cognitive loss. However, complications were also associated with the vaccine compositions since CTL mediated meningoencephalitis occurred some immunized AD patients (Schenk, 2002; Rosenberg, 2005). Given these results it would be highly desirable to develop an Aβ vaccine that can effectively reduce Aβ plaques without inducing a CTL (i.e. Th1 type immune) response. However, despite the description of a number of possible Aβ vaccine compositions there has not been a vaccine composition able to induce an therapeutic antibody response while not stimulating a strong CTL immune response that can lead to encephalitis.

Figure 1:
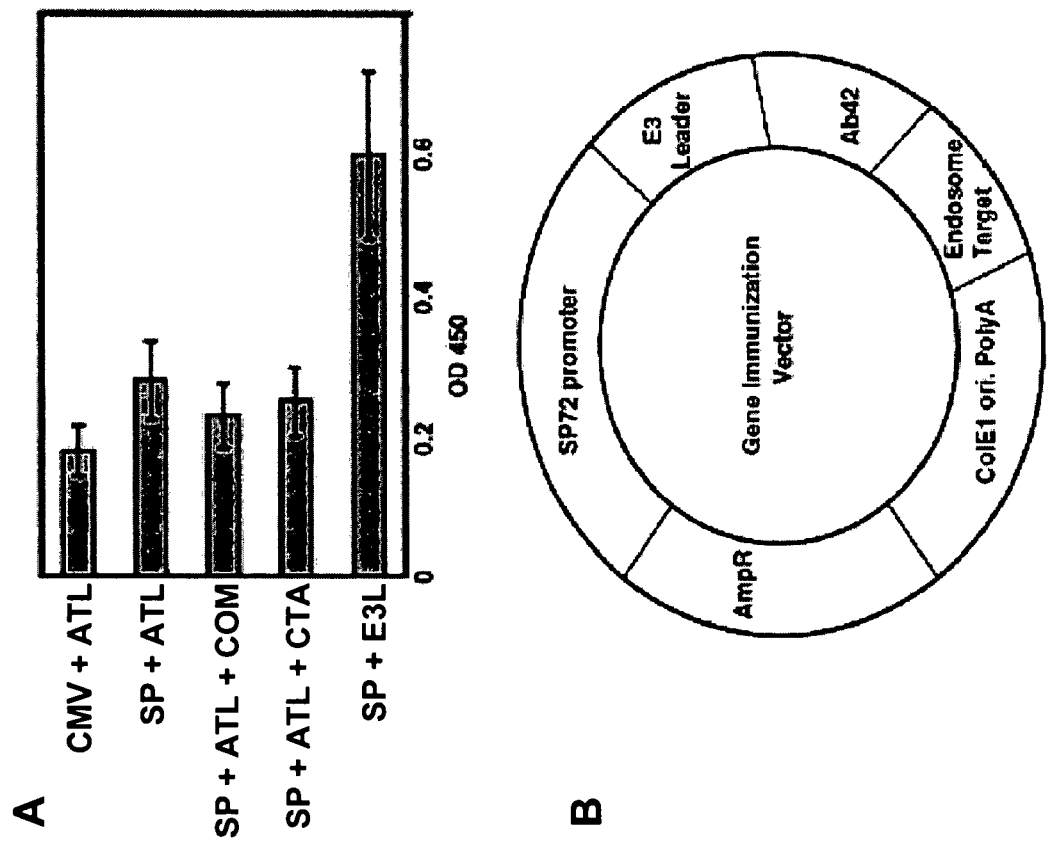
FIG. 1A-B: A, Aβ peptide specific immune responses in BALB/c wild-type mice immunized with human Aβ42 gene vaccine cloned in the indicated vectors (n=3). Serum is obtained 14 days after the second vaccination and analyzed at a dilution of 1:200. The serum is tested by ELISA for Aβ42 peptide. Vector used for vaccination are essentially as depicted in FIG. 1B however the promoter (CMV or SP72 (SP)) and leader sequence (E3L or ATL) for each tested construct is indicated on the left. Additionally, the B-cell targeted CTA1-DD gene (CTA) or the rat cartilage oligomerization matrix protein gene (COM) is inserted between the leader and Aβ42 in two of the vectors as indicted. Mice vaccinated with pSP-E3L-Aβ42 have the highest anti-Aβ42 antibody titer. B, a schematic representation of the basic DNA construct sequence. The adenovirus E3 leader, Aβ42 or Aβ16 peptides, and endosome targeting peptide are cloned in frame under the control of a synthetic SP72 mammalian cell-specific promoter.
Figure 2:
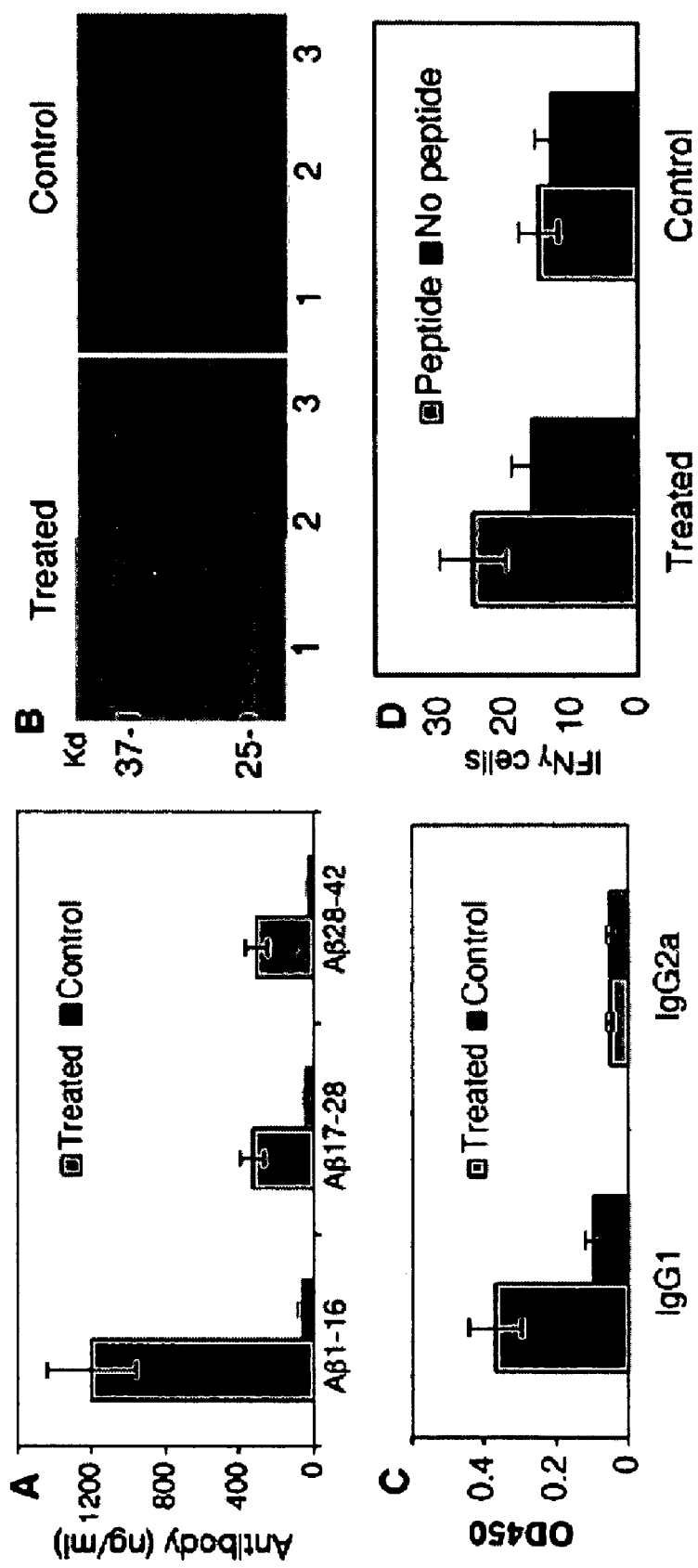
FIG. 2A-D: Human Aβ42 specific immune responses in APPswe/PS1ΔE9 double transgenic mice immunized with human Aβ42 gene vaccine. A, anti-Aβ peptide antibody titer assayed by ELISA in mice immunized with Aβ42, 6 times over a four month period. The serum is obtained 2 weeks after the 6th immunization and titers are tested against GST fused Aβ peptide 1-16, 17-28, 29-42. Higher titers against Aβ 1-16 are observed relative to the other epitopes (the bar value represent mean±S.E.M. of four mice). B, the same serum (as in FIG. 2A) tested with Western blot shows a similar result, with a higher response against the Aβ1-16 epitope. The sera from control mice are negative. Lane 1: Aβ1-16, lane 2: Aβ17-28, lane 3: Aβ29-42 peptide fused to GST is loaded and probed with the serum in 1:2000 dilution. C, isotyping of anti-Aβ42 antibodies after immunization of mice with pSP72-E3L-Aβ42. The sera is diluted 1:200 and used for detection of IgG1, IgG2a subclasses of anti-Aβ42 antibodies. All mice demonstrated an IgG1 (Th2) response without detectable IgG2a (Th1) response (mean±S.E.M., n=4). D, ELISPOT assay shows that no significant cellular immune response is observed in human Aβ42 gene vaccinated mice. Peripheral blood T cells are pooled from the vaccinated and vector only control mice and the cells were cultured in quadruplicate ($2\times10^5$ cells per well in 96-well plate format) in the presence or absence of Aβ peptide using a mixture of Aβ42 and Aβ9-18 peptide at 10 µg/ml for 36 h and further processed for detection of released interferon. Control mice in each case (FIG. 2A-D) receive vector only construct without any Aβ gene insert which induce no detectable specific anti-Aβ antibodies in sera and no significant cellular immune response.

The studies detailed herein demonstrate that Aβ gene vaccination can elicit a strong Th2 immune response to Aβ and that such an immune response may be useful for treating Alzheimer's disease. Various DNA constructs are tested as genetic vaccines to determine the optimal sequence for generating an antibody response to Aβ in mice. Studies presented in FIG. 1A show that DNA vectors comprising an adenovirus E3L sequence, Aβ42 and an endosomal targeting sequence are the most effective at inducing a high titer antibody response. Importantly, the antibody response primarily comprises IgG1 rather than IgG2a antibodies (FIG. 2C). This antibody profile indicates that the response is a Th2 type immune response and suggests that the vaccine may not elicit a strong CTL response. This finding is confirmed by the ELISPOT CTL assays present in FIG. 2D which indicates a very low level CTL response. Together these studies demonstrate that Aβ nucleic acid vaccines may have improved safety relative to the vaccines that have been previously available, nonetheless the vaccines are able to induce a significant Aβ-antibody response.

Figure 3:
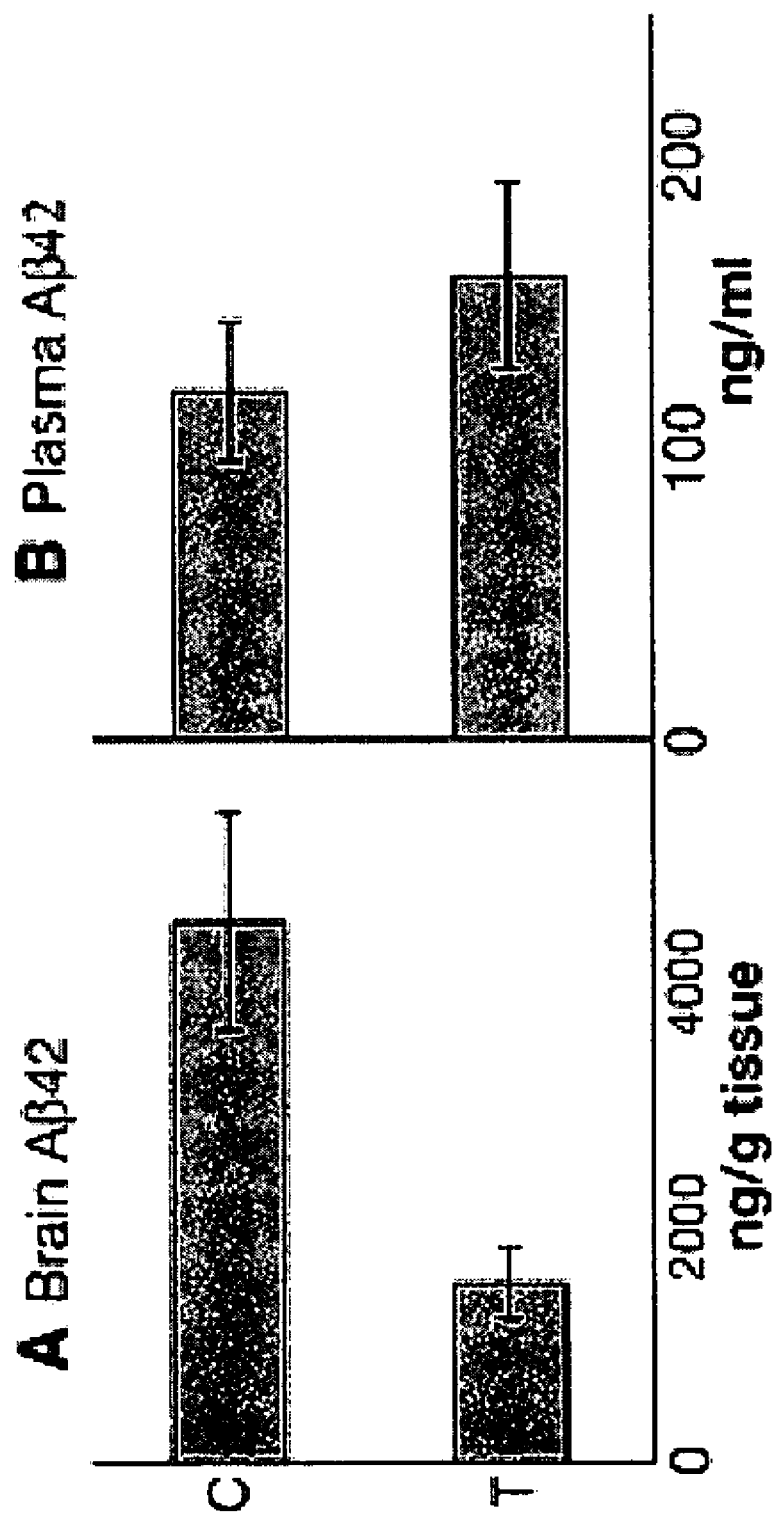
FIG. 3A-B: Levels of Aβ42 in forebrain (A) and in plasma (B) of 15-month-old APPswe/PS1ΔE9 transgenic mice treated with the Aβ42 gene vaccine (T) (n=4) or control (C) (2 mice with Aβ16 construct (T) and 2 mice vector only(C)). Bars represent mean±S.E.M. of four mice in both groups. A, the forebrain is extracted with 5 M guanidine-tris buffer and Aβ42 is quantified by sandwich ELISA. There is about 70% reduction of total Aβ42 in the forebrain of vaccinated mice compared to the control. B, plasma samples are diluted in 1:100 in blocking buffer and Aβ42 levels are measured by sandwich ELISA.
Figure 4:
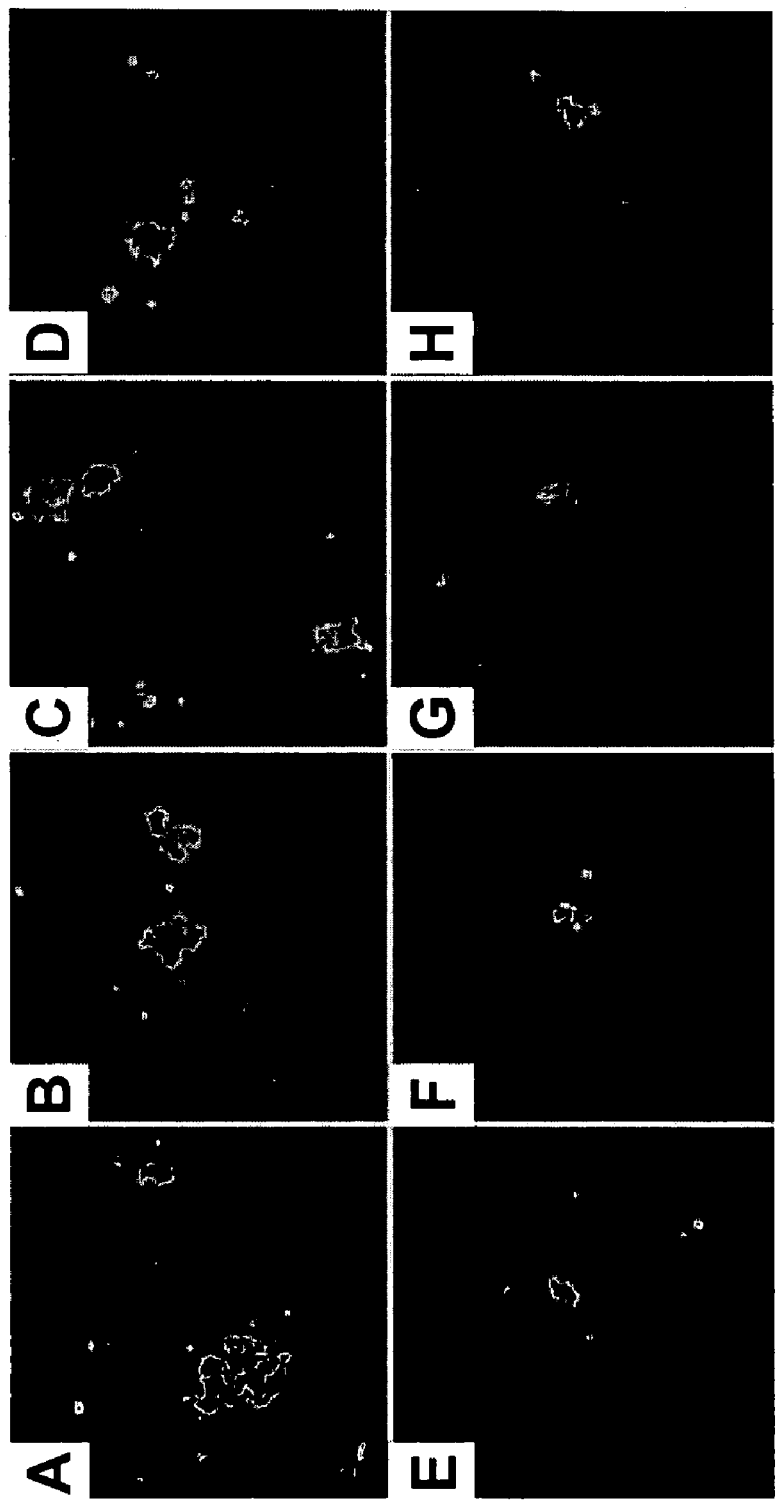

Since these new Aβ gene vaccines may have enhanced safety (i.e. induce a Th2 rather than a Th1 immune response) further studies are presented that demonstrate efficacy of the compositions. Results shown in FIG. 3, indicate that vaccinated mice have a reduce Aβ concentrations in the brain, a marker that has been associate with improved cognitive function. Nonetheless, serum levels of Aβ vaccinated animal virtually unchanged or slightly elevated indicating that the Aβ protein may be cleared from the brain tissue into the blood. Further analyses shown in FIG. 4 and FIG. 5 further demonstrate that Aβ plaques in the brain are also reduced in density and size. Taken together these studies indicate that the Aβ gene vaccines provided, herein not only produce an immune response that is safer, but also are effective in reducing the Aβ in the brain tissues of afflicted animals.

In view of the studies presented here it is clear that compositions and methods of the invention provide new methods for Aβ vaccination and genetic vaccines that may be used to treat or prevent Alzheimer's disease. The genetic vaccines described here stimulate a Th2 type immune response resulting in robust production of anti-Aβ antibodies, while minimizing production of anti-Aβ CTLs. These vaccines are able to reduce Aβ plaques in the brains of animals, in some cases reducing the concentration of brain Aβ by 60%. Furthermore, Aβ antigens that are fused to an adenoviral leader sequence provide more effective vaccine vectors for use in therapy since these vectors elicit significantly more Aβ specific IgG1 antibodies as compared to other vaccine vectors. Thus, new methods for treating and preventing Alzheimer's disease are provided that induce a Th2 type Aβ immune response thereby reducing Aβ protein levels in the brain.

I. Nucleic Acids

The present invention concerns a number of different types of nucleic acid molecules that can be used in a variety of ways. In some embodiments of the invention, the nucleic acid is a recombinant nucleic acid. The term "recombinant" is used according to its ordinary and plain meaning to refer to the product of recombinant DNA technology, e.g., genetically engineered DNA prepared in vitro by cutting up DNA molecules and splicing together specific DNA fragments, which may or may not be from different organisms. Things that have or are from a genetically engineered DNA are similarly recombinant; this includes replicated or duplicated products based on the initially engineered DNA. In particular embodiments, the invention concerns therapeutic nucleic acids recombinant DNA and RNA molecules.

1. Antigen Mutagenesis

In particular embodiments, antigenic compositions such as Aβ fusion proteins are mutated for purposes such as, enhancing immunogenicity or producing or identifying a immunologically functional equivalent sequence. Methods of mutagenesis are well known to those of skill in the art (Sambrook et al., 1987). In some cases, the mutagenesis may be specifically directed, for example to introduce mutations into Aβ (e.g., mutations found in AD patients). Methods for such mutagenesis are detailed below.

As used herein, the term "oligonucleotide directed mutagenesis procedure" refers to template dependent processes and vector mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template dependent extension of a primer molecule. The term template dependent process refers to nucleic acid synthesis of an RNA or a DNA molecule wherein the sequence of the newly synthesized strand of nucleic acid is dictated by the well known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

For instance, in a some embodiments, site directed mutagenesis is used. Site specific or site directed mutagenesis is a technique useful in the preparation of an antigenic composition (e.g., an Aβ fusion protein or immunologically functional equivalent protein, polypeptide or peptide), through specific mutagenesis of the underlying DNA. In general, the technique of site specific mutagenesis is well known in the art. The technique further provides a ready ability to prepare and test sequence variants, incorporating one or more of the foregoing considerations, by introducing one or more nucleotide sequence changes into the DNA. Site-specific mutagenesis allows the production of a mutant through the use of specific oligonucleotide sequence(s) which encode the DNA sequence of the desired mutation, as well as a sufficient number of adjacent nucleotides, to provide a primer sequence of sufficient size and sequence complexity to form a stable duplex on both sides of the position being mutated. Typically, a primer of about 17 to about 75 nucleotides in length is preferred, with about 10 to about 25 or more residues on both sides of the position being altered, while primers of about 17 to about 25 nucleotides in length being more preferred, with about 5 to 10 residues on both sides of the position being altered.

In a specific example of site-specific mutagenesis, a pair of primers may be annealed to two separate strands of a double stranded vector to simultaneously synthesize both corresponding complementary strands with the desired mutation(s) in a PCR™ reaction. A genetic selection scheme to enrich for clones incorporating the mutagenic oligonucleotide has been devised (Kunkel et al., 1987). Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector (Tomic et al., 1990; Upender et al., 1995). A PCR™ employing a thermostable ligase in addition to a thermostable polymerase also may be used to incorporate a phosphorylated mutagenic oligonucleotide into an amplified DNA fragment that may then be cloned into an appropriate cloning or expression vector.

The preparation of sequence variants of the selected gene/antigen using site directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

As discussed above in certain aspects of the invention, it will be understood that the sequence of an Aβ fusion protein may be modified by amino substitutions. For example, an amino acid at one or more positions may be exchanged with an amino acid having a similar hydrophilicity (see above). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made Aβ fusion protein and such substitutions will likely only have minor effects on protein antigenicity. For instance, substitution of amino acids whose hydrophilicity values are within ±2 are preferred, those that are within ±1 are particularly preferred, and those within ±0.5 are even more particularly preferred. Thus, any of the polypeptide domains described herein may be modified by the substitution of an amino acid, for a different, but homologous amino acid with a similar hydrophilicity value. Amino acids with hydrophilicities within +/−1.0, or +/−0.5 points are considered homologous.

In certain embodiments, a peptide or polypeptide may contain an amino acid sequence that is identical or similar to a reference sequence or a particular region of the reference sequence (e.g, an E3L or Aβ amino acid sequence). In certain embodiments a peptide or polypeptide has at least or most 60, 65, 70, 75, 80, 85, 90, 95, 96, 97, 98, 99, 99.5, 100% identity with respect to the amino acid sequence of a particular polypeptide or within a region of the particular polypeptide.

2. Vectors

In order to effect replication, expression or mutagenesis of a nucleic acid, the nucleic acid may be delivered ("transfected") into a cell. The tranfection of cells may be used, in certain embodiments, to recombinately produce one or more vaccine components for subsequent purification and preparation into a pharmaceutical vaccine. In other embodiments, the nucleic acid may be comprised as a genetic vaccine that is administered to an animal. In other embodiments, the nucleic acid is transfected into a cell and the cell administered to an animal as a cellular vaccine component. The nucleic acid may consist only of naked recombinant DNA, or may comprise, for example, additional materials to protect the nucleic acid and/or aid its targeting to specific cell types.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell.

The nucleic acid encoding the antigenic composition or other vaccine component may be stably integrated into the genome of the cell, or may be stably maintained in the cell as a separate, episomal segment of DNA. Such nucleic acid segments or "episomes" encode sequences sufficient to permit maintenance and replication independent of or in synchronization with the host cell cycle. Vectors and expression vectors may contain nucleic acid sequences that serve other functions as well and are described infra. How the expression construct is delivered to a cell and where in the cell the nucleic acid remains is dependent on the type of expression construct employed.

a. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, http://www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

In addition to the promoters exemplified herein (i.e., CMV and SP72) a multitude of other promoter may be used in compositions of the instant invention. Table 1 lists non-limiting examples of elements/promoters that may be employed, in the context of the present invention, to regulate the expression of a RNA. Table 2 provides non-limiting examples of inducible elements, which are regions of a nucleic acid sequence that can be activated in response to a specific stimulus.

TABLE 1

| Promoter/Enhancer | Promoter and/or Enhancer References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |

TABLE 1-continued

Promoter and/or Enhancer

| Promoter/Enhancer | References |
| --- | --- |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $α_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | Poly(rI)x Poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Nonlimiting examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), and human platelet endothelial cell adhesion molecule-1 (Almendro et al., 1996).

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. Since the context of the translation initiation codon in also important, in some aspects a polypeptide coding sequence may be mutated in order to improve the context of the ATG (Kozak, 1986). The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

e. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

g. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

h. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

i. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, $E.$ $coli$ is often transformed using derivatives of pBR322, a plasmid derived from an $E.$ $coli$ species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEMTM 11 may be utilized in making a recombinant phage vector which can be used to transform host cells, such as, for example, $E.$ $coli$ LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with β galactosidase, ubiquitin, and the like.

Bacterial host cells, for example, $E.$ $coli$, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

j. Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Aβ vaccine components of the present invention may be a viral vector that encode for example an Aβ fusion protein or other components such as, for example, an immunomodulator or adjuvant. Nonlimiting examples of virus vectors that may be used to deliver a nucleic acid of the present invention are described below.

i. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

ii. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the Aβ vaccines of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

iii. Retroviral Vectors

Retroviruses have promise as Aβ fusion protein delivery vectors in Aβ vaccines due to their ability to integrate their genes into the host genome, transferring a large amount of foreign genetic material, infecting a broad spectrum of species and cell types and of being packaged in special cell lines (Miller, 1992).

In order to construct a Aβ vaccine retroviral vector, a nucleic acid (e.g., one encoding an Aβ fusion protein of interest) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

iv. Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

v. Vaccine Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989). Thus, it is contemplated that antibodies, specific binding ligands and/or other targeting moieties may be used to specifically transfect APC types.

II. Vaccine Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215; incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium mediated transformation (U.S. Pat. Nos. 5,591,616 and 5,563,055, each incorporated herein by reference); or by PEG mediated transformation of protoplasts (Omirulleh et al., 1993; U.S. Pat. Nos. 4,684,611 and 4,952,500, each incorporated herein by reference); by desiccation/inhibition mediated DNA uptake (Potrykus et al., 1985), and any combination of such methods. Through the application of techniques such as these, organelle(s), cell(s), tissue(s) or organism(s) may be stably or transiently transformed.

1. Injection

In certain embodiments, a nucleic acid may be delivered to an organelle, a cell, a tissue or an organism via one or more injections (i.e., a needle injection). Methods of injection of nucleic acids are described herein, and are well known to those of ordinary skill in the art. Further embodiments of the present invention include the introduction of a nucleic acid by direct microinjection to a cell. Direct microinjection has been used to introduce nucleic acid constructs into Xenopus oocytes (Harland and Weintraub, 1985). The amount of Aβ encoding nucleic acid used may vary upon the nature of the antigen as well as the organelle, cell, tissue or organism used 2. Electroporation In certain embodiments of the present invention, a nucleic acid is introduced into an organelle, a cell, a tissue or an organism via electroporation. Electroporation involves the exposure of a suspension of cells and DNA to a high voltage electric discharge. In some variants of this method, certain cell wall degrading enzymes, such as pectin degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre B lymphocytes have been transfected with human kappa immunoglobulin genes (Potter et al., 1984), and rat hepatocytes have been transfected with the chloramphenicol acetyltransferase gene (Potter et al., 1984) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

3. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV 1, BHK, NIH3T3 and HeLa cells were transfected with a neomycin marker gene (Chen and Okayama, 1987), and rat hepatocytes were transfected with a variety of marker genes (Rippe et al., 1990).

4. DEAE Dextran

In another embodiment, a nucleic acid is delivered into a cell using DEAE dextran followed by polyethylene glycol. In this manner, reporter plasmids were introduced into mouse myeloma and erythroleukemia cells (Gopal, 1985).

5. Sonication Loading

Additional embodiments of the present invention include the introduction of a nucleic acid by direct sonic loading. LTK fibroblasts have been transfected with the thymidine kinase gene by sonication loading (Fechheimer et al., 1987).

6. Liposome Mediated Transfection

In a further embodiment of the invention, one or more vaccine components or nucleic acids may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome mediated nucleic acid delivery and expression of foreign DNA in vitro has been very successful (Nicolau and Sene, 1982; Fraley et al., 1979; Nicolau et al., 1987). The feasibility of liposome mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome encapsulated DNA (Kaneda et al., 1989). In other embodiments, a liposome may be complexed or employed in conjunction with nuclear non histone chromosomal proteins (HMG 1) (Kato et al., 1991). In yet further embodiments, a liposome may be complexed or employed in conjunction with both HVJ and HMG 1. In other embodiments, a delivery vehicle may comprise a ligand and a liposome.

7. Receptor Mediated Transfection

One or more vaccine components or nucleic acids, may be employed to delivered using a receptor mediated delivery vehicle. These take advantage of the selective uptake of macromolecules by receptor mediated endocytosis that will be occurring in the target cells. In view of the cell type specific distribution of various receptors, this delivery method adds another degree of specificity to the present invention. Specific delivery in the context of another mammalian cell type has been described (Wu and Wu, 1993, incorporated herein by reference).

Certain receptor mediated gene targeting vehicles comprise a cell receptor specific ligand and a nucleic acid binding agent. Others comprise a cell receptor specific ligand to which the nucleic acid to be delivered has been operatively attached. Several ligands have been used for receptor mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell specific binding. For example, lactosyl ceramide, a galactose terminal asialganglioside, have been incorporated into liposomes and observed an increase in the uptake of the insulin gene by hepatocytes (Nicolau et al., 1987). It is contemplated that the tissue specific transforming constructs of the present invention can be specifically delivered into a target cell in a similar manner.

8. Microprojectile Bombardment

As specifically exemplified herein, microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA coated microprojectiles (e.g., gold particles) to a high velocity allowing them to pierce cell membranes and enter cells without killing them (Klein et al., 1987). There are a wide variety of microprojectile bombardment techniques known in the art, many of which are applicable to the invention.

Microprojectile bombardment may be used to transform various cell(s), tissue(s) or organism(s), such as for example any plant species. Examples of species which have been transformed by microprojectile bombardment include monocot species such as maize (PCT Application WO 95/06128), barley (Ritala et al., 1994; Hensgens et al., 1993), wheat (U.S. Pat. No. 5,563,055, incorporated herein by reference), rice (Hensgens et al., 1993), oat (Torbet et al., 1995; Torbet et al., 1998), rye (Hensgens et al., 1993), sugarcane (Bower et al., 1992), and sorghum (Casas et al., 1993; Hagio et al., 1991); as well as a number of dicots including tobacco (Tomes et al., 1990; Buising and Benbow, 1994), soybean (U.S. Pat. No. 5,322,783, incorporated herein by reference), sunflower (Knittel et al. 1994), peanut (Singsit et al., 1997), cotton (McCabe and Martinell, 1993), tomato (Van Eck et al. 1995), and legumes in general (U.S. Pat. No. 5,563,055, incorporated herein by reference).

In this microprojectile bombardment, one or more particles may be coated with at least one nucleic acid and delivered into cells by a propelling force such as pressurized gas. Several devices for accelerating small particles have been developed. One such device relies on a high voltage discharge to generate an electrical current, which in turn provides the motive force (Yang et al., 1990). Another device the Helios gene gun (Bio-Rad, Hercules, Calif.; Gilman et al., 2005) used pressurized gas (e.g., helium) as a propelling force. The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA coated particles may increase the level of DNA delivery via particle bombardment but are not, in and of themselves, necessary.

III. Additional Vaccine Components

It is contemplated that an antigenic composition of the invention may be combined with one or more additional components to form a more effective vaccine. Non-limiting examples of additional components include, for example, one or more additional antigens, immunomodulators or adjuvants to stimulate an immune response to an antigenic composition of the present invention and/or the additional component(s). As used herein the terms immunomodulator and immune modifiers are used interchangeably.

1. Immunomodulators

For example, it is contemplated that immunomodulators can be included in the vaccine to augment a cell's or a patient's (e.g., an animal's) response. Immunomodulators can be included as purified proteins, nucleic acids encoding immunomodulators, and/or cells that express immunomodulators in the vaccine composition. In some cases an immunemodulators may be used to bias an immune response by, for example, specifically stimulating a Th2 immune response. For instance DNA vector encoding IRF-1 can increases Th2 antibody responses (Sasaki et al., 2002). The following sections list non-limiting general examples of immunomodulators that are of interest, and it is contemplated that various combinations of immunomodulators may be used in certain embodiments (e.g., a cytokine and a chemokine).

a. Cytokines

Interleukins, cytokines, nucleic acids encoding interleukins or cytokines, and/or cells expressing such compounds are contemplated as possible vaccine components. Interleukins and cytokines, include but are not limited to interleukin 1 (IL-1), IL-2, IL-3, IL-4, IL-5, IL-18, β-interferon, α-interferon, γ-interferon, angiostatin, thrombospondin, endostatin, GM-CSF, G-CSF, M-CSF, METH 1, METH 2, tumor necrosis factor, TGFβ, LT or antibodies to any of the foregoing.6, IL-7, IL-8, IL-9, IL-10, IL-11, IL-12, IL-13, IL-14, IL-15, IL b. Chemokines Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-alpha, MIP1-Beta, IP-10 and combinations thereof. The skilled artisan will recognize that certain cytokines are also known to have chemoattractant effects and could also be classified under the term chemokines.

c. Immunogenic Carrier Proteins

In certain embodiments, an antigenic composition may be chemically coupled to a carrier or recombinantly expressed with a immunogenic carrier peptide or polypetide (e.g., a antigen-carrier fusion peptide or polypeptide) to enhance an immune reaction. Exemplary and preferred immunogenic carrier amino acid sequences include hepatitis B surface antigen, keyhole limpet hemocyanin (KLH) and bovine serum albumin (BSA). Other albumins such as ovalbumin, mouse serum albumin or rabbit serum albumin also can be used as immunogenic carrier proteins. Means for conjugating a polypeptide or peptide to a immunogenic carrier protein are well known in the art and include, for example, glutaraldehyde, m maleimidobenzoyl N hydroxysuccinimide ester, carbodiimide and bis biazotized benzidine.

d. Biological Response Modifiers

It may be desirable to coadminister biologic response modifiers (BRM), which have been shown to upregulate T cell immunity or downregulate suppressor cell activity. Such BRMs include, but are not limited to, cimetidine (CIM; 1200 mg/d) (Smith/Kline, PA); low dose cyclophosphamide (CYP; 300 mg/m2) (Johnson/Mead, NJ), or a gene encoding a protein involved in one or more immune helper functions, such as B 7.

2. Adjuvants

Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation.

In one aspect, an adjuvant effect is achieved by use of an agent, such as alum, used in about 0.05 to about 0.1% solution in phosphate buffered saline. Alternatively, the antigen is made as an admixture with synthetic polymers of sugars (Carbopol®) used as an about 0.25% solution. Adjuvant effect may also be made my aggregation of the antigen in the vaccine by heat treatment with temperatures ranging between about 70° to about 101° C. for a 30 second to 2 minute period, respectively. Aggregation by reactivating with pepsin treated (Fab) antibodies to albumin, mixture with bacterial cell(s) such as C. parvum, an endotoxin or a lipopolysaccharide component of Gram negative bacteria, emulsion in physiologically acceptable oil vehicles, such as mannide mono oleate (Aracel A), or emulsion with a 20% solution of a perfluorocarbon (Fluosol DA®) used as a block substitute, also may be employed.

Some adjuvants, for example, certain organic molecules obtained from bacteria, act on the host rather than on the antigen. An example is muramyl dipeptide (N acetylmuramyl L alanyl D isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen specific. If they are administered together with a purified antigen, however, they can be used to selectively promote the response to the antigen.

3. Vaccine Preparations

Once produced, synthesized and/or purified, an antigen or other vaccine component may be prepared as a vaccine for administration to a patient. The preparation of a vaccine is generally well understood in the art, as exemplified by U.S. Pat. Nos. 4,608,251, 4,601,903, 4,599,231, 4,599,230, and 4,596,792, all incorporated herein by reference. Such methods may be used to prepare a vaccine comprising an Aβ fusion protein gene as active ingredient(s), in light of the present disclosure. In preferred embodiments, the compositions of the present invention are prepared to be pharmacologically acceptable vaccines.

Pharmaceutical vaccine compositions of the present invention comprise an effective amount of one or more Aβ nucleic acid sequences or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one Aβ nucleic acid or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). An Aβ vaccine composition may comprise different types of carriers depending on whether it is to be administered in solid, liquid or aerosol form, and whether it need to be sterile for such routes of administration as injection. Except insofar as any conventional carrier is incompatible with the active ingredient, its use in the therapeutic or pharmaceutical compositions is contemplated.

In any case, the composition may comprise various antioxidants to retard oxidation of one or more component and/or prevent nucleolytic degradation. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the Aβ vaccine is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

IV. Vaccine Administration

The manner of administration of a vaccine may be varied widely. Any of the conventional methods for administration of a vaccine are applicable. For example, a vaccine may be conventionally administered intravenously, intradermally, intraarterially, intraperitoneally, intralesionally, intracranially, intraarticularly, intraprostaticaly, intrapleurally, intratracheally, intranasally, intravitreally, intravaginally, intratumorally, intramuscularly, intraperitoneally, subcutaneously, intravesicularlly, mucosally, intrapericardially, orally, rectally, nasally, topically, in eye drops, locally, using aerosol, injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

A vaccination schedule and dosages may be varied on a patient by patient basis, taking into account, for example, factors such as the weight and age of the patient, the type of disease being treated, the severity of the disease condition, previous or concurrent therapeutic interventions, the manner of administration and the like, which can be readily determined by one of ordinary skill in the art.

A vaccine is administered in a manner compatible with the dosage formulation, and in such amount as will be therapeutically effective and immunogenic. For example, the intramuscular route may be preferred in the case of toxins with short half lives in vivo. The quantity to be administered depends on the subject to be treated, including, e.g., the capacity of the individual's immune system to synthesize antibodies, and the degree of protection desired. The dosage of the vaccine will depend on the route of administration and will vary according to the size of the host. Precise amounts of an active ingredient required to be administered depend on the judgment of the practitioner. In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein However, a suitable dosage range may be, for example, of the order of several hundred micrograms active ingredient per vaccination. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per vaccination, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. A suitable regime for initial administration and booster administrations (e.g., inoculations) are also variable, but are typified by an initial administration followed by subsequent inoculation(s) or other administration(s).

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1 5 years, usually three years, will be desirable to maintain protective levels of the antibodies.

The course of the immunization may be followed by assays for antibodies for the supernatant antigens, such as those exemplified herein. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays. For example, assays may be performed to determine the relative Th1/Th2 character of the immune response. For example, an immune response may be monitored with a FAST® Quant Human Th1/Th2 protein array available from Whatman. This assays enables quantitation of a variety of serum marker for immune response and can be used to closely monitor the immune response.

EXAMPLES

The following examples are included to further illustrate various aspects of the invention. It should be appreciated by those of skill in the art that the techniques disclosed in the examples that follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

DNA Constructs and Cloning

The Aβ42 or Aβ16 genes are cloned into a genetic immunization plasmid vector essentially as described in Qu et al., 2004 (FIG. 1B). The Aβ42 and Aβ16 genes are fused to an upstream leader signal from the adenovirus E3 gene (E3L) (pSP72-E3L-Aβ42 or Aβ16) or the alpha1 antitrypsin leader signal (ATL) (pSP72-ATL-Aβ42) (Ciernik et al., 1996). The E3L sequence is identical to the adenovirus type 2 sequence used in Ciernik et al., 1996 however the AUG consensus sequence has been improved resulting a signal amino acid substitution (compare SEQ ID NO: 10 to SEQ ID NO: 3). In each case a lysosome targeting sequence is fused downstream of the Aβ42 and Aβ16 sequences (Qu et al., 2004; Marques et al., 2003; Chen et al., 1985). Additionally, in certain constructs, the B-cell targeted CTA1-DD gene or the rat cartilage oligomerization matrix protein (COMP) gene is inserted between the leader and Aβ42 or Aβ16 to create the plasmids designated pSP72-ATL-COM-Aβ42 and SP72-ATL-CTA1-Aβ42 (Chambers & Johnston 2003; Eriksson & Lycke 2003). As discussed in Eriksson & Lycke 2003, the CTA1-DD gene is a fusion between the ADP-ribosylation domain of cholera toxin and an Ig-binding fragment D of *Staphylococcus aureus* protein A. In each cases expression of the indicated fusion protein is under the control of a synthetic mammalian-cell specific promoter SP72, however in the test construct pCMV-ATL-Aβ42 the SP72 is replaced with the cytomegalovirus-immediate early enhancer/promoter (CMV) in order to test the effect of the two different promoters.

Example 2

DNA Immunization of Balb/c Mice

Initially, 5-7 week old wild type Balb/c mice (obtained from Harlan Inc., Indianapolis, Ind.) are immunized with the indicted plasmid constructs by gene gun to compare the efficiency inducing a Aβ42 immune response. The immunizations are performed on mouse ear skin using the Helios gene gun (Bio-Rad, Hercules, Calif.) as described (Gilman et al., 2005). Briefly, DNA-coated gold particles are prepared by binding DNA to the gold beads (1-2 μm, Ferro Electronic Material Systems, South Plainfield, N.J.) in 1 μg DNA/1 mg gold beads in the presence of spermidine and calcium chloride. The DNA-gold is attached to the insides of the tubing and cut into 1.3 cm long as a bullet. Next, the DNA-coated gold particles are bombarded to both sides of the mouse ears using the gene gun powered by 400 psi helium gas. After two gene gun immunizations separated by 2-week intervals, tail vein blood is taken (blood draw is 2 weeks after the second immunization) and ELISA is performed using 96-microwell plates coated with GST-Aβ protein to measure the anti-Aβ antibodies in sera. To determine the specific antibody isotypes in the sera, samples for ELISA were diluted 1:200 and detected by Ig-subclass-specific (IgG1 or IgG2a) rabbit antibody (Pierce, Rockford, Ill.), followed by incubation with HRP-conjugated Donkey anti-rabbit IgG.

Results from these immunization experiments indicate that pSP72-E3L-Aβ42 construct shows the best antibody response. Fusion of the putative adjuvant sequences, COM or CTA1-DD, to Aβ does not enhance the humoral immune responses against Aβ peptide. The SP72 promoter appears slightly more effective than CMV. Interestingly, the adenovirus E3 leader is significantly better than the AAT leader sequence at inducing a humoral immune response (FIG. 1A). These result these results indicate that the SP72-E3L-Aβ42 plasmid may be an excellent candidate for gene immunization in APPswe/PS1ΔE9 transgenic mice.

Example 3

DNA Immunization of APPswe-PS1ΔE9 Mice

On the basis of data from injection of wild-type Balb/c mice, the pSP72-E3L-Aβ42 construct is used for gene-gun immunization in APP/PS1 co-injected double transgenic mice APPswe/PS1ΔE9 from Jackson Laboratory (Bar Harbor, Me.) (Stock Number 004462). These mice carry the human APP-Swedish and PS1ΔE9 mutations and begin to develop amyloid plaques in the cerebral cortex and hippocampus by the age of 6 months. Plasmids are administered on mouse ear skin using the Helios gene gun as described above. Four treated mice are administered the human Aβ42 gene vaccine at the age of 3 months and four control mice are administered DNA plasmid without the Aβ peptide gene (2) or with the Aβ16 gene (2). The humoral response is detectable by ELISA two weeks after the third immunization and reached a peak level after six immunizations. The antibody titer against Aβ1-16 is estimated at 1:10,000 and 1:4000 for Aβ17-28 and Aβ29-42 peptides in all four treated Tg mice. There are no detectable specific anti-Aβ antibodies in the sera of vector only control Tg mice. Results of ELISA and Western blots (FIGS. 2A and 2B) show similar conclusions. FIG. 2A shows the antibody concentrations of the sera of Aβ42 treated mice obtained 2 weeks after the last immunization with about 1.2 µg/ml specific anti-Aβ1-16 antibodies and 350 ng/ml of anti-Aβ17-28 and Aβ29-42.

The isotype of anti-Aβ42 antibodies in the sera of Aβ42 treated Tg mice is also analyzed. All treated Tg mice generate IgG1 antibodies, whereas the level of IgG2a is in an undetectable level (FIG. 2C). The production of IgG1 antibodies is an indirect measure of the relative contribution of Th2-type cytokines, whereas IgG2a antibodies reflect the contribution of Th1 cytokines to the immune response. Thus, these data indicate that gene gun mediated Aβ42 gene vaccine gun induces a highly Th2-polarized response. Consistent with the Th2 response in antibody isotyping, these Aβ42 treated mice also show insignificant cellular immune responses as tested by ELISPOT stimulated with Aβ1-42 and Aβ9-18 synthetic peptide although a slightly higher number of interferon positive T cells is observed (FIG. 2D).

ELISA and Western Blot Analysis

Enzyme-linked immunoabsorbent assay (ELISA) and Western blot are used to monitor the humoral immune responses (Qu et al., 2004). In each case, mouse blood is collected from tail vein and serum is used to detect Aβ peptide by ELISA with 96-microwell plate coated with GST-Aβ proteins. For Western blot, the GST-Aβ proteins in bacteria extract are separated by SDS-PAGE, blotted onto nitrocellulose, and incubated with the sera at 1:2000 dilutions. Antibodies against Aβ are detected using peroxidase-conjugated affinity-purified rabbit antiserum against mouse Ig. To determine the specific isotypes, sera from mice were diluted 1:200 and tested with ELISA method as described above. To detect mouse IgG1, IgG2a, we used anti-mouse Ig-subclass-specific rabbit antibody (Pierce, Rockford, Ill.), followed by incubation with HRP-conjugated Donkey anti-rabbit IgG (FIG. 2C).

ELISPOT Analysis

The cell-mediated immune response is evaluated by enzyme-linked immunospot assays (ELISPOT assay) for detection of peripheral blood T cell to release interferon-γ during in vitro re-stimulation with Aβ peptide (Kumar et al., 2001). Briefly, 96-well polyvinylidine diflouride (PVDF) plates (Millipore, Bedford, Mass.) are coated with antibody to IFN-γ. Cells were cultured at $2 \times 10^5$ per well in 0.2 ml of medium for re-stimulation with Aβ peptides. After 36 hours of incubation at 37° C., the plates are washed, incubated with biotinylated anti-mouse IFN-gamma, and further with Streptavidin-AP conjugate. After three washes, spots are developed with one-step NBT/BCIP reagent. Spots are counted using a stereomicroscope and the results graphed (FIG. D).

Example 4

DNA Immunization Reduces the Amount of Aβ in Brain Tissue

After 11 Aβ42 gene vaccinations, the Aβ ELISA analysis is performed to measure the brain and blood Aβ42 levels in 15-month-old Tg mice. The Aβ of forebrain tissue is extracted with 5 M guanidine-tris buffer and subjected to sandwich ELISA to measure the specific Aβ42. The median level of Aβ42 in the cerebral cortex of the four control mice at 15 months is 4500 ng/g wet tissue. In contrast, Aβ42 gene vaccinated animals have 66% less Aβ42 at 15 months (1500 ng/g) than the control vector immunized group ($p<0.05$) (FIG. 3A). The heparinized plasma is directly subjected to Aβ42 measurement without further extraction and shows a 33% increase of plasma Aβ42 in the vaccinated mice (160 ng/ml) than the four control mice (120 ng/ml), though these differences are not statistically different (FIG. 3B).

ELISA Analysis of Aβ from Brain Tissue

The frontal lobe of brain is homogenized in 10 volumes of guanidine-tris buffer (5.0 M guanidine HCl/50 mM Tris-HCl, pH 8.0). The homogenates are mixed for 3 to 4 h at room temperature (RT) and stored at −20° C. until measured (Vanderstichele et al., 2000 and (Johnson-Wood et al., 1997). For ELISA assay, 96-well plates (Nunc) are coated with polyclonal antibody (50 µl, 1:400 dilutions) that specifically recognize the C-terminal of Aβ42 (Sigma) at 4° C. overnight. The plate is further blocked by adding 100 µl blocking buffer (PBS with 1% milk, 0.05% Tween 20) for 2 hours in RT. After washing with washing buffer (PBS containing 0.05% Tween 20), the brain extracts in guanidine buffer (4 µg protein per µl) or the plasma are diluted in 1:100 in blocking buffer and added to the well. The plate is incubated overnight in 4° C. After washing, 50 µl of monoclonal anti-Aβ1-17 antibody (Sigma, 1:1000 in blocking buffer) is added to the well to detect the bound Aβ42. After 2 a hour incubation in RT, 50 µl of peroxidase-labeled anti-mouse immunoglobulin antibody (dilution of 1:1000) is added to each well. Following 2-hour incubation and washing, 50 µl of substrate solution (TMB, Calbiochem, La Jolla, Calif.) is added and terminated after 20 min RT incubation with 50 µl 0.5 M HCl. ELISA analysis of serum Aβ concentrations are performed as outlined above. Different concentrations (1-2000 ng/ml) of synthetic Aβ42 peptide were used to establish the standard curve. The absorbance of the plates is read at 450 nm with a spectrophotometer and the results graphed (FIG. A-B).

Example 5

Analysis of Aβ Plaques in the Brains of Immunized Mice

Figure 5:
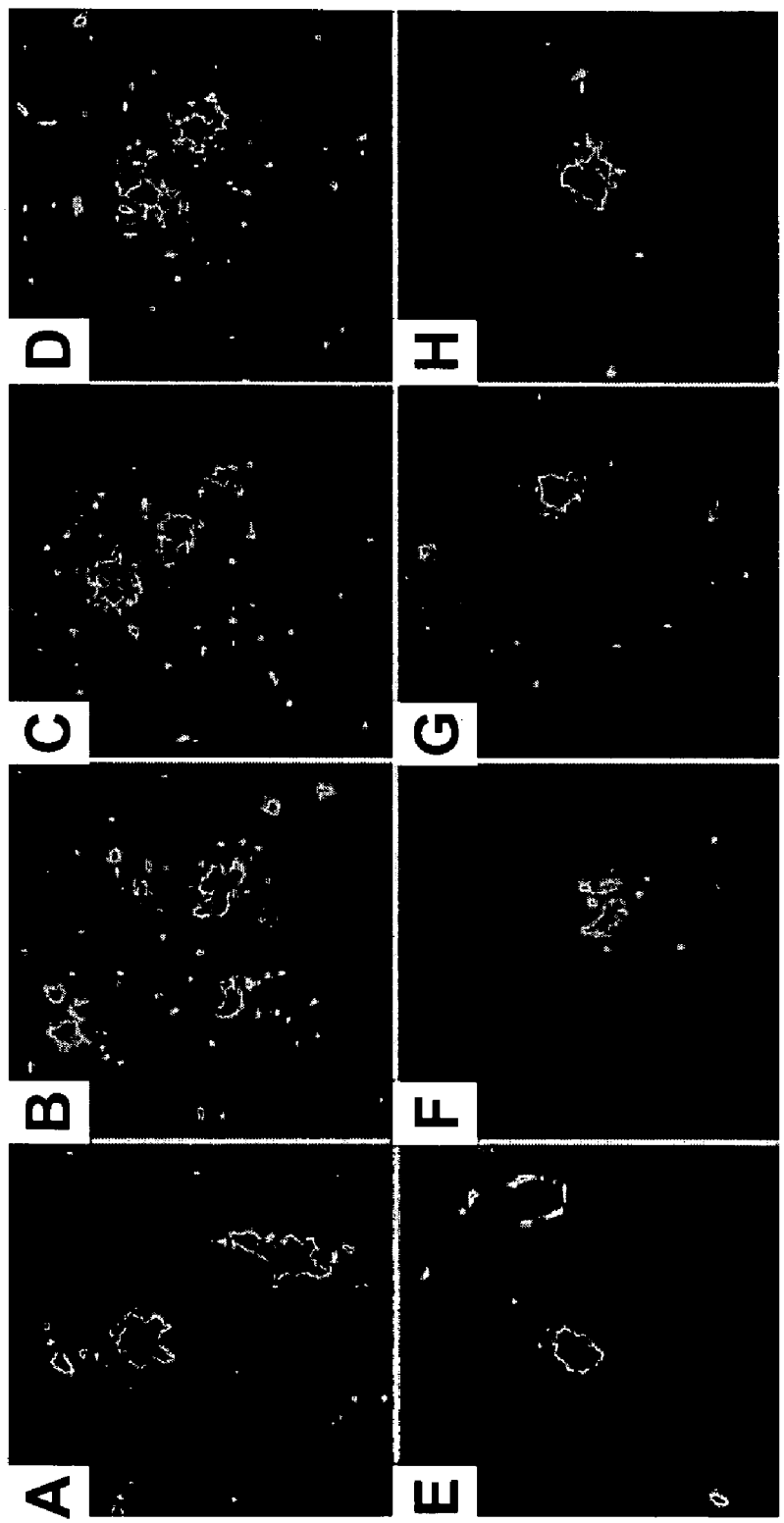

To evaluate the Aβ burden in vaccinated Tg mouse brain, Aβ42 immunolabeling is proformed on sections from both snap frozen tissue and paraformaldehyde fixed and paraffin embedded tissue. All eight mice (treated N=4, and control N=4) are subjected to immunolabeling analysis for Aβ42 with sigma antibody A1916. Preparations from all four control mice show numerous large volume plaques in cortical and hippocampal regions. In contrast, while plaques remain in preparations from all four vaccinated mice, they are smaller and fewer in number. Representative photomicroimages of Aβ42 labelled sections from control and treated mice are shown in frozen sections of frontal cortex (FIG. 4) and in paraformaldehyde fixed paraffin-embedded sections from hippocampus (FIG. 5). To quantitatively measure the brain Aβ42 burden in these mice, 10 representative high-resolution pictures are taken with confocal microscopy from cortical and hippocampal regions of each mouse (5 in frozen sections and 5 in paraffin-embedded sections). The fluorescence plaque areas of each microimage are traced by Image J (NIH) software and the plaque areas and mean plaque intensity are registered by the software. The plaque intensity is defined as 0 in black and 255 in white and the fluorescence intensity is registered as a gray signal in between. The fluorescence plaque areas are registered in units of pixels, a small dot defined by the software and computer, in a given resolution. The density (total amount) is given by the measured plaque area in pixels multiplied by the average plaque intensity. With this method is used to quantitatively evaluated the plaque burden in brain and calculated the reduction of Aβ42 in treated mice compared to the untreated control mice. The measured values are given in Table 3 and Table 4.

Table 3 shows the quantitative result of frozen sections and Table 4 of paraffin-embedded sections. With frozen sectioning methods, the median plaque area of four control mice with five imaged areas being measured in each mouse is 177,100 pixels and 31,500 pixels in the four treated mice. The plaque area is reduced by 82.2% in the treated compared to the control mice. Similarly, the median density of four control mice (25.3 million pixels) is also significantly reduced in the treated mice (5.7 million pixels) with a Mann-Whitney P=0.0286. There is a 77.5% reduction in plaque burden in treated mice as calculated by plaque density (total amount) (Table 3). The same method is used to measure the Aβ42 burden reduction in the vaccinated mice brains in paraffin-embedded sections. The median plaque volume in four control mice is 201,600 pixels and 69,100 pixels in four vaccinated mice with a 65.7% reduction in plaque area in the treated mice. The median plaque density (total amount) of the control mice is 35.3 million pixels and 14.2 million pixels in the treated mice. The reduction of the plaque burden in the treated mice is 60% as calculated by the plaque density(total amount) with a Mann-Whitney P=0.0286 (Table 4). In conclusion, with Image J software quantitation of Aβ42 burden in a total of 80 representative confocal imaged areas (40 in control and 40 in treated mice), the reduction of Aβ42 burden is 60-77.5% in the gene vaccinated group of mice compared to the control group of mice. Both tissue processing methods give the same conclusion and there is no overlap of the data between the control and treated groups both for frozen and paraffin-embedded brain for Aβ42 levels. Sections from one control and one treated mouse which included formic antigen retrieval methodology were studied with Image J software.

Formic acid antigen retrieval is commonly employed in the diagnostic evaluation of human AD brain tissue for Aβ levels. The median plaque density (total amount) of the vector only control mouse (C1) frontal cortex is 36.2 million pixels and the median plaque density (total amount) of the treated mouse (T2) frontal cortex is 21.6 million pixels, giving a 41% reduction in Aβ42 immunolabelling. This additional evaluation is included to assure quantitation of all potential amyloid antigenicity and demonstration of significant reduction in Aβ42 immunolabelling in the treated mouse brain. In addition, the immune response induced by gene vaccination to Aβ42 does not produce any obvious signs of damage to the neurons in Aβ42 gene-immunized animals. Histological examination of brain revealed no signs of immune-mediated complications. The weight gain is similar in both groups with an average 40 g body weight at 15 months of age.

TABLE 3

| Mice | Sum of plaque area ($\times 10^3$) | Mean of plaque intensity | Plaque density ($\times 10^6$) (total amount) |
|---|---|---|---|
| C1 | 221.7 | 169.7 | 37.6 |
| C2 | 200.5 | 141.9 | 28.5 |
| C3 | 153.7 | 144.5 | 22.2 |
| C4 | 148.9 | 145.9 | 21.7 |
| Median C1-4 | 177.1* | 145.2 | 25.3* |
| T1 | 66.1 | 166.3 | 11.0 |
| T2 | 26.0 | 86.1 | 2.2 |
| T3 | 20.0 | 181.4 | 3.6 |
| T4 | 37.0 | 207.7 | 7.7 |
| Median T1-4 | 31.5* (17.8%) | 173.8 | 5.7* (22.5%) |

TABLE 4

| Mice | Sum of plaque area ($\times 10^3$) | Mean of plaque intensity | Plaque density ($\times 10^6$) (total amount) |
|---|---|---|---|
| C1 | 288.5 | 210.1 | 60.6 |
| C2 | 179.7 | 185.2 | 33.3 |
| C3 | 219.3 | 168.8 | 37.0 |
| C4 | 183.8 | 182.3 | 33.5 |
| Median C1-4 | 201.6* | 183.7 | 35.3* |
| T1 | 57.0 | 223.8 | 12.8 |
| T2 | 45.1 | 212.1 | 9.6 |
| T3 | 81.1 | 193.3 | 15.7 |
| T4 | 88.3 | 205.3 | 18.1 |
| Median T1-4 | 69.1* (34.3%) | 208.7 | 14.2* (40.2%) |

Immunofluorescence Analysis of Brain Sections

Portions of the brain from APPswe/PS1ΔE9 transgenic mice are dissected and put into a tube filled with PBS and the tube is snap frozen in liquid nitrogen. Part of the brain is also fixed with paraformaldehyde and embedded in paraffin. The frozen tissues are subsequently cut into 8-μm sections with a cryotome, collected on glass slides, dried and fixed for 4 h in 4% paraformaldehyde. After washing with PBS, the section is penetrated with 0.2% Triton X-100 for 10 min and further washed and blocked with blocking buffer (1% BSA in PBS with 0.05% Tween 20) for 30 min. After incubation with rabbit polyclonal anti-serum (Borchelt et al., 1997) (A1916, Sigma, St. Louis, Mo.) against Aβ42 (5 μg/ml, 2 h at RT), the sections are washed three times for 5 min each in PBS, again treated with blocking buffer (5 min, RT) before reacting with the secondary antibody (Alexa488-labeled goat anti-rabbit IgG, (10 μg/ml, 1 h, RT) (Invitrogen Co.; Carlsbad, Calif.).

Finally, the preparations are washed three times in PBS and observed by confocal fluorescence microscopy. The amyloid plaque burden is analyzed with Image J (NIH) software. Five representative sections of each mouse brain are imaged and the areas and densities of the plaques are measured by the software. Sections from paraffin embedded tissue (8 µm) are deparaffinized and immunolabeled as above. In addition, formic acid antigen retrieval is performed on sections of frontal cortex from one control and one treated mouse and stained as above.

Statistical Analysis

Because the assumptions of the two independent samples t-test are violated (unequal group variances and non-normal distributions), quantitative measurement of Aβ42 burden in frozen and paraffin-embedded sections for control and treatment groups are compared using the non-parametric Mann-Whitney U-test. Analyses are performed using SAS and statistical testing is conducted using $p<0.05$.

REFERENCES

The following references, to the extent that they provide exemplary procedural or other details supplementary to those set forth herein, are specifically incorporated herein by reference.

U.S. Pat. No. 3,791,932
U.S. Pat. No. 3,949,064
U.S. Pat. No. 4,174,384
U.S. Pat. No. 4,196,265
U.S. Pat. No. 4,237,224
U.S. Pat. No. 4,554,101
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,683,202
U.S. Pat. No. 4,683,202
U.S. Pat. No. 4,684,611
U.S. Pat. No. 4,797,368
U.S. Pat. No. 4,952,500
U.S. Pat. No. 5,139,941
U.S. Pat. No. 5,302,523
U.S. Pat. No. 5,322,783
U.S. Pat. No. 5,322,783
U.S. Pat. No. 5,354,855
U.S. Pat. No. 5,384,253
U.S. Pat. No. 5,464,765
U.S. Pat. No. 5,466,468
U.S. Pat. No. 5,538,877
U.S. Pat. No. 5,538,880
U.S. Pat. No. 5,538,880
U.S. Pat. No. 5,550,318
U.S. Pat. No. 5,563,055
U.S. Pat. No. 5,563,055
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,610,042
U.S. Pat. No. 5,620,479
U.S. Pat. No. 5,656,610
U.S. Pat. No. 5,693,762
U.S. Pat. No. 5,702,932
U.S. Pat. No. 5,736,524
U.S. Pat. No. 5,780,448
U.S. Pat. No. 5,789,215
U.S. Pat. No. 5,846,225
U.S. Pat. No. 5,846,233
U.S. Pat. No. 5,861,021
U.S. Pat. No. 5,861,155
U.S. Pat. No. 5,922,013
U.S. Pat. No. 5,925,565
U.S. Pat. No. 5,928,906
U.S. Pat. No. 5,928,906
U.S. Pat. No. 5,935,819
U.S. Pat. No. 5,945,100
U.S. Pat. No. 5,981,274
U.S. Pat. No. 5,994,136
U.S. Pat. No. 5,994,624
U.S. Pat. No. 6,013,516
U.S. Pat. No. 6,020,192
U.S. Pat. No. 6,054,297
U.S. Pat. No. 6,114,175
U.S. Pat. No. 6,167,313
U.S. Pat. No. 6,168,776
U.S. Pat. No. 6,417,178
U.S. Pat. No. 6,787,140
U.S. Pat. No. 6,852,834
U.S. Publn. 2004/0091945
U.S. Publn. 2004/0138296
U.S. Publn. 2004/0171573
U.S. Publn. 20030059944
U.S. Publn. 20030105051
Almendro et al., *J. Immunol.*, 157(12):5411-5421, 1996.
Angel et al., *Cell*, 49:729, 1987b.
Angel et al., *Mol. Cell. Biol.*, 7:2256, 1987a.
Atchison and Perry, *Cell*, 46:253, 1986.
Atchison and Perry, *Cell*, 48:121, 1987.
Ausubel et al., In: *Current Protocols in Molecular Biology*, John, Wiley & Sons, Inc, New York, 1994.
Baichwal and Sugden, In: *Gene Transfer*, Kucherlapati (Ed.), NY, Plenum Press, 117-148, 1986.
Banerji et al., *Cell*, 27(2 Pt 1):299-308, 1981.
Banerji et al., *Cell*, 33(3):729-740, 1983.
Bates, *Mol. Biotechnol.*, 2(2):135-145, 1994.
Battraw and Hall, *Theor. App. Genet.*, 82(2):161-168, 1991.
Berkhout et al., *Cell*, 59:273-282, 1989.
Bhattacharjee et al., *J. Plant Bioch. Biotech.*, 6(2):69-73. 1997.
Blanar et al., *EMBO J.*, 8:1139, 1989.
Blomer et al., *J. Virol.*, 71(9):6641-6649, 1997.
Bodine and Ley, *EMBO J.*, 6:2997, 1987.
Borchelt et al., *Neuron*, 19:939-945, 1997.
Boshart et al., *Cell*, 41:521, 1985.
Bosze et al., *EMBO J.*, 5(7):1615-1623, 1986.
Bower et al., *Plant J.*, 2:409-416. 1992.
Braddock et al., *Cell*, 58:269, 1989.
Buising and Benbow, *Mol. Gen. Genet.*, 243(1):71-81, 1994.
Bulla and Siddiqui, *J. Virol.*, 62:1437, 1986.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Carbonelli et al., *FEMS Microbiol. Lett.*, 177(1):75-82, 1999.
Casas et al., *Proc. Natl. Acad. Sci. USA*, 90(23):11212-11216, 1993.
Celander and Haseltine, *J. Virology*, 61:269, 1987.
Celander et al., *J. Virology*, 62:1314, 1988.
Chambers and Johnston, *Nat. Biotechnol.*, 9:1088-1092, 2003.
Chambers and Johnston, *Nat. Biotechnol.*, 9:1088-1092, 2003.

Chandler et al., *Cell*, 33:489, 1983.
Chandler et al., *Proc. Natl. Acad. Sci. USA*, 94(8):3596-601, 1997.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell Biol.*, 7(8):2745-2752, 1987.
Chen et al., *J. Cell Biol.* 101:85-95, 1985.
Choi et al., *Cell*, 53:519, 1988.
Christou et al., *Proc. Natl. Acad. Sci. USA*, 84(12):3962-3966, 1987.
Ciernik et al., *J. Immunol.*, 156:2369-2375, 1996.
Ciernik et al., *J. Immunol.*, 156:2369-2375, 1996.
Cocea, *Biotechniques*, 23(5):814-816, 1997.
Cohen et al., *J. Cell. Physiol.*, 5:75, 1987.
Costa et al., *Mol. Cell. Biol.*, 8:81, 1988.
Cotten et al., *Proc. Natl. Acad. Sci. USA*, 89(13):6094-6098, 1992.
Coupar et al., *Gene*, 68:1-10, 1988.
Cripe et al., *EMBO J.*, 6:3745, 1987.
Culotta and Hamer, *Mol. Cell. Biol.*, 9:1376, 1989.
Curiel, 1994
Dandolo et al., *J. Virology*, 47:55-64, 1983.
De Villiers et al., *Nature*, 312(5991):242-246, 1984.
DeMattos et al., *Proc. Natl. Acad. Sci. USA*, 98:8850-8855, 2001.
Deschamps et al., *Science*, 230:1174-1177, 1985.
Edbrooke et al., *Mol. Cell. Biol.*, 9:1908, 1989.
Edlund et al., *Science*, 230:912-916, 1985.
EPO 0273085
Eriksson and Lycke, *Vaccine*, 22:185-193, 2003.
Eriksson and Lycke, *Vaccine*, 22:185-193, 2003.
Fechheimer, et al., *Proc Natl. Acad. Sci. USA*, 84:8463-8467, 1987.
Feng and Holland, *Nature*, 334:6178, 1988.
Firak and Subramanian, *Mol. Cell. Biol.*, 6:3667, 1986.
Foecking and Hofstetter, *Gene*, 45(1):101-105, 1986.
Fox et al., *Biochem. Biophys. Res. Commun.*, 240:759-762, 1997.
Fox et al., *Neurology*, 64:1563-1572, 2005.
Fraley et al., *Proc. Natl. Acad. Sci. USA*, 76:3348-3352, 1979.
Friedmann, *Science*, 244:1275-1281, 1989.
Fujita et al., *Cell*, 49:357, 1987.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gilles et al., *Cell*, 33:717, 1983.
Gilman et al., *Neurology*, 64:1553-1562, 2005.
Gilman et al., *Neurology*, 64:1553-1562, 2005.
Gloss et al., *EMBO J.*, 6:3735, 1987.
Godbout et al., *Mol. Cell. Biol.*, 8:1169, 1988.
Goodbourn and Maniatis, *Proc. Natl. Acad. Sci. USA*, 85:1447, 1988.
Goodbourn et al., *Cell*, 45:601, 1986.
Gopal, *Mol. Cell Biol.*, 5:1188-1190, 1985.
Graham and Van Der Eb, *Virology*, 52:456-467, 1973.
Greene et al., *Immunology Today*, 10:272, 1989
Grosschedl and Baltimore, *Cell*, 41:885, 1985.
Grunhaus and Horwitz, *Seminar in Virology*, 3:237-252, 1992.
Haass et al., *Nature*, 359:322-325, 1992.
Hagio et al., *Plant Cell Rep.*, 10(5):260-264, 1991.
Harland and Weintraub, *J. Cell Biol.*, 101(3):1094-1099, 1985.
Haslinger and Karin, *Proc. Natl. Acad. Sci. USA*, 82:8572, 1985.
Hauber and Cullen, *J. Virology*, 62:673, 1988.
He et al., *Plant Cell Reports*, 14 (2-3):192-196, 1994.
Hen et al., *Nature*, 321:249, 1986.
Hensel et al., *Lymphokine Res.*, 8:347, 1989.
Hensgens et al., *Plant Mol. Biol.*, 22(6):1101-1127, 1993.
Herr and Clarke, *Cell*, 45:461, 1986.
Hirochika et al., *J. Virol.*, 61:2599, 1987.
Hirsch et al., *Mol. Cell. Biol.*, 10:1959, 1990.
Hock et al., *Neuron.*, 38:547-554, 2003.
Holbrook et al., *Virology*, 157:211, 1987.
Horlick and Benfield, *Mol. Cell. Biol.*, 9:2396, 1989.
Horwich et al. *J. Virol.*, 64:642-650, 1990.
Hou and Lin, *Plant Physiology*, 111:166, 1996.
Huang et al., *Cell*, 27:245, 1981.
Hug et al., *Mol. Cell. Biol.*, 8:3065, 1988.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Inouye and Inouye, *Nucleic Acids Res.*, 13: 3101-3109, 1985.
Iwatsubo et al., *Ann. Neurol.*, 37:294-299, 1995.
Iwatsubo et al., *Neuron.*, 13z;45-53, 1994.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9:3393, 1989.
Johnson-Wood et al., *Proc. Natl. Acad. Sci. USA*, 94:1550-1555, 1997.
Kadesch and Berg, *Mol. Cell. Biol.*, 6:2593, 1986.
Kaeppler et al., *Plant Cell Rep.*, 8:415-418, 1990.
Kaneda et al., *Science*, 243:375-378, 1989.
Karin et al., *Mol. Cell. Biol.*, 7:606, 1987.
Karin et al., *Mol Cell. Biol.*, 7:606, 1987.
Katinka et al., *Cell*, 20:393, 1980.
Kato et al, *J. Biol. Chem.*, 266:3361-3364, 1991.
Kawamoto et al., *Mol. Cell. Biol.*, 8:267, 1988.
Kelleher and Vos, *Biotechniques*, 17(6):1110-7, 1994.
Kiledjian et al., *Mol. Cell. Biol.*, 8:145, 1988.
Klamut et al., *Mol. Cell. Biol.*, 10:193, 1990.
Klein et al., *Nature*, 327:70-73, 1987.
Klunk et al., *Ann. Neurol.*, 55:306-319, 2004
Knittel et al., *Plant Cell Reports*, 14(2-3):81-86, 1994.
Koch et al., *Mol. Cell. Biol.*, 9:303, 1989.
Kotilinek et al., *J. Neurosci.*, 22:6331-6335, 2002.
Kozak, *Cell* 44:283-292, 1986.
Kozak, *J. Mol. Biol.*, 196:947-950, 1987.
Kozak, *Mol Cell. Biol.*, 9:5073-5080, 1989.
Kraus et al. *FEBS Lett.*, 428(3):165-170, 1998.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kumar et al., *J. Immunol. Methods*, 247:49-60, 2001.
Kunkel et al., *Methods Enzymol.*, 154:367-382, 1987.
Kunz et al., *Nucl. Acids Res.*, 17:1121, 1989.
Lahiri and Ge, Ann. NY Acad. Sci., 1030:310-316, 2004.
Lareyre et al., *J. Biol. Chem.*, 274(12):8282-8290, 1999.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Laughlin et al., *J. Virol.*, 60(2):515-524, 1986.
Lazzeri, *Methods Mol. Biol.*, 49:95-106, 1995.
Lebkowski et al., *Mol. Cell. Biol.*, 8(10):3988-3996, 1988.
Lee et al., *Biochem. Biophys. Res. Commun.*, 238(2):462-467, 1997.

Lee et al., *Environ. Mol. Mutagen.*, 13(1):54-59, 1989.
Lee et al., *Nature*, 294:228, 1981.
Lee et al., *Nucleic Acids Res.*, 12:4191-206, 1984.
Levenson et al., *Hum. Gene Ther.*, 9(8):1233-1236, 1998.
Levinson et al., *Nature*, 295:79, 1982.
Lin et al., *Mol. Cell. Biol.*, 10:850, 1990.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Sarnow, *Nature*, 353:90-94, 1991.
Majors and Varmus, *Proc. Natl. Acad. Sci. USA*, 80:5866, 1983.
Maniatis, et al., Molecular Cloning, A Laboratory Manual, Cold Spring Harbor Press, Cold Spring Harbor, N.Y., 1988.
Mann et al., *Cell*, 33:153-159, 1983.
Marques Jr., et al., *J. Biol. Chem.*, 278:37926-37936, 2003.
Marques Jr., et al., *J. Biol. Chem.*, 278:37926-37936, 2003.
McCabe and Martinell, *Bio-Technology*, 11(5):596-598, 1993.
McLaughlin et al., *J. Virol.*, 62(6):1963-1973, 1988.
McNeall et al., *Gene*, 76:81, 1989.
Miksicek et al., *Cell*, 46:203, 1986.
Miller et al., *Am. J. Clin. Oncol.*, 15(3):216-221, 1992.
Monsonego and Weiner, *Science*, 302:834-838, 2003.
Mordacq and Linzer, *Genes and Dev.*, 3:760, 1989.
Moreau et al., *Nucl. Acids Res.*, 9:6047, 1981.
Morgan et al., *Nature*, 408:982-985, 2000.
Muesing et al., *Cell*, 48:691, 1987.
Muzyczka, *Curr. Topics Microbiol. Immunol.*, 158:97-129, 1992.
Naldini et al., *Science*, 272(5259):263-267, 1996.
Ng et al., *Nuc. Acids Res.*, 17:601, 1989.
Nicolas and Rubinstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
Nicolau et al., *Methods Enzymol.*, 149:157-176, 1987.
Nomoto et al., *Gene*, 236(2):259-271, 1999.
Omirulleh et al., *Plant Mol. Biol.*, 21(3):415-28, 1993.
Ondek et al., *EMBO J.*, 6:1017, 1987.
Ornitz et al., *Mol. Cell. Biol.*, 7:3466, 1987.
Palmiter et al., *Nature*, 300:611, 1982.
Paskind et al., *Virology*, 67:242-248, 1975.
PCT Appln. 95/06128
PCT Appln. WO 2005/014041
PCT Appln. WO 9217598
PCT Appln. WO 94/09699
PCT Appln. WO 94/09699
PCT Appln. WO 95/06128
PCT Appln. WO 99/27944
PCT Appln. WO 99/27944
PCT Appln. WO 99/27944
Pech et al., *Mol. Cell. Biol.*, 9:396, 1989.
Pelletier and Sonenberg, *Nature*, 334(6180):320-325, 1988.
Perales et al., *Proc. Natl. Acad. Sci. USA*, 91:4086-4090, 1994.
Perez-Stable and Constantini, *Mol. Cell. Biol.*, 10:1116, 1990.
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potrykus et al., *Mol. Gen. Genet.*, 199(2):169-177, 1985.
Potter et al., *Proc. Natl. Acad. Sci. USA*, 81:7161-7165, 1984.
Qu et al., *Arch. Neurol.*, 61:1859-1864, 2004.
Qu et al., *Arch. Neurol.*, 61:1859-1864, 2004.
Queen and Baltimore, *Cell*, 35:741, 1983.
Quinn et al., *Mol. Cell. Biol.*, 9:4713, 1989.
Redondo et al., *Science*, 247:1225, 1990.
Reisman and Rotter, *Mol. Cell. Biol.*, 9:3571, 1989.
Remington's Pharmaceutical Sciences, 18th Ed. Mack Printing Company, pp. 1289-1329, 1990.
Resendez Jr. et al., *Mol. Cell. Biol.*, 8:4579, 1988.
Ridgeway, In: *Vectors: A Survey of Molecular Cloning Vectors and Their Uses*, Rodriguez et al. (Eds.), Stoneham: Butterworth, 467-492, 1988.
Ripe et al., *Mol. Cell. Biol.*, 9:2224, 1989.
Rippe, et al., *Mol. Cell Biol.*, 10:689-695, 1990.
Ritala et al., *Plant Mol. Biol.*, 24(2):317-325, 1994.
Rittling et al., *Nuc. Acids Res.*, 17:1619, 1989.
Rosen et al., *Cell*, 41:813, 1988.
Rosenberg, *JAMA*, 294:2352-2353, 2005.
Rosenberg, *Neurology*, 54:2045-2054, 2000.
Roux et al., *Proc. Natl. Acad. Sci. USA*, 86:9079-9083, 1989.
Sakai et al., *Genes and Dev.*, 2:1144, 1988.
Sambrook et al., In: *Molecular cloning: a laboratory manual*, $2^{nd}$ Ed., Cold Spring Harbor Laboratory Press, Cold Spring Harbor, N.Y., 1987.
Sambrook et al., *In: Molecular cloning: a laboratory manual*, $2^{nd}$ Ed., Cold Spring Harbor Laboratory Press, Cold Spring Harbor, N.Y., 1989.
Sasaki et al., *Mol. Cancer Ther.*, 1(13):1201-1209, 2002.
Satake et al., *J. Virology*, 62:970, 1988.
Schaffner et al., *J. Mol. Biol.*, 201:81, 1988.
Schenk et al., *Nature*, 400:173-177, 1999.
Schenk, *Nat. Rev. Neurosci.*, 3:824-828, 2002.
Searle et al., *Mol. Cell. Biol.*, 5:1480, 1985.
Selkoe, *Nature*, 399:A23-A31, 1999.
Selkoe, *Physiol. Rev.*, 81:741-766, 2001.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Shoji et al., *Science*, 258:126-129, 1992.
Singsit et al., *Transgenic Res.*, 6(2):169-176, 1997.
Sleigh and Lockett, *J. EMBO*, 4:3831, 1985.
Sorbi, *Neurol. Sci.*, 26(Suppl. 1):S5, 2005.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati (Ed.), NY, Plenum Press, 149-188, 1986.
Thiesen et al., *J. Virology*, 62:614, 1988.
Tomes et al., *Plant. Mol. Biol.*, 14(2):261-268, 1990.
Tomic et al., *Nucl. Acids Res.*, 12:1656, 1990.
Torbet et al., *Crop Science*, 38(1):226-231, 1998.
Torbet et al., *Plant Cell Reports*, 14(10):635-640, 1995.
Tratschin et al., *Mol. Cell. Biol.*, 4:2072-2081, 1984.
Treisman, *Cell*, 42:889, 1985.
Tronche et al., *Mol. Biol. Med.*, 7:173, 1990.
Trudel and Constantini, *Genes and Dev.*, 6:954, 1987.
Tsukada et al., *Plant Cell Physiol.*, 30(4)599-604, 1989.
Tsumaki et al., *J. Biol. Chem.*, 273(36):22861-22864, 1998.

Tur-Kaspa et al., *Mol. Cell Biol.*, 6:716-718, 1986.
Tyndell et al., *Nuc. Acids. Res.*, 9:6231, 1981.
Upender et al., *Biotechniques*, 18:29-31, 1995.
Van Eck et al., *Plant Cell Reports*, 14(5):299-304, 1995.
Vanderstichele et al., *Amyloid*, 7:245-258, 2000.
Vannice and Levinson, *J. Virology*, 62:1305, 1988.
Vasseur et al., *Proc Natl. Acad. Sci. USA*, 77:1068, 1980.
Wagner et al., *Proc. Natl. Acad. Sci. USA* 87(9):3410-3414, 1990.
Wang and Calame, *Cell*, 47:241, 1986.
Watson et al., *In: Molecular Biology of the Gene*, 4th Ed., W. A. Benjamin, Inc., Menlo Park, Calif., 1987.
Weber et al., *Cell*, 36:983, 1984.
Weinberger et al. *Mol. Cell. Biol.*, 8:988, 1984.
Winoto and Baltimore, *Cell*, 59:649, 1989.
Wong et al., *Gene*, 10:87-94, 1980.
Wu and Wu, *Adv. Drug Delivery Rev.*, 12:159-167, 1993.
Wu and Wu, *Biochemistry*, 27: 887-892, 1988.
Wu and Wu, *J. Biol. Chem.*, 262:4429-4432, 1987.
Wu et al., *Biochem. Biophys. Res. Commun.*, 233(1):221-226, 1997.
Yang and Russell, *Proc. Natl. Acad. Sci. USA*, 87:4144-4148, 1990.
Yankner, *Neuron.*, 16:921-932, 1996.
Yutzey et al. *Mol. Cell. Biol.*, 9:1397, 1989.
Zhao-Emonet et al., *Biochim. Biophys. Acta*, 1442(2-3):109-119, 1998.
Zufferey et al., *Nat. Biotechnol.*, 15(9):871-875, 1997.

What is claimed is:

1. A nucleic acid encoding a fusion protein comprising the amino acid sequence of SEQ ID NO: 4.

2. A method for stimulating a Th2 immune response against an Aβ polypeptide in an animal comprising administering to the animal a nucleic acid encoding a fusion protein comprising the amino acid sequence of SEQ ID NO: 4, wherein the Th2 immune response against the Aβ polypeptide is stimulated.

3. The method of claim 2, further comprising administering the nucleic acid to the animal a second time.

4. The method of claim 2, wherein the nucleic acid is bound to gold particles.

5. The method of claim 2, wherein the nucleic acid is administered with a gene gun.

* * * * *